US008624055B2

(12) United States Patent
Schammel et al.

(10) Patent No.: US 8,624,055 B2
(45) Date of Patent: *Jan. 7, 2014

(54) PROCESS AND CATALYST FOR OXIDIZING AROMATIC COMPOUNDS

(75) Inventors: Wayne P. Schammel, Plainfield, IL (US); Bradley J. Huggins, Sugar Grove, IL (US); Matthew A. Kulzick, Warrenville, IL (US); Philip O. Nubel, Naperville, IL (US); Bryan M. Rabatic, Naperville, IL (US); Chengxiang Zhou, Lisle, IL (US); Victor A. Adamian, Naperville, IL (US); William H. Gong, Elmhurst, IL (US); Peter D. Metelski, Bollingbrook, IL (US); Jeffrey T. Miller, Naperville, IL (US)

(73) Assignee: BP Corporation North America Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/598,902

(22) PCT Filed: May 1, 2008

(86) PCT No.: PCT/US2008/062130
§ 371 (c)(1),
(2), (4) Date: Nov. 4, 2009

(87) PCT Pub. No.: WO2008/137491
PCT Pub. Date: Nov. 13, 2008

(65) Prior Publication Data
US 2010/0145094 A1  Jun. 10, 2010

Related U.S. Application Data

(60) Provisional application No. 60/986,180, filed on Nov. 7, 2007, provisional application No. 60/987,996, filed on Nov. 14, 2007.

(30) Foreign Application Priority Data

May 4, 2007  (WO) ................ PCT/US2007/068261
May 4, 2007  (WO) ................ PCT/US2007/068268
May 4, 2007  (WO) ................ PCT/US2007/068274

(51) Int. Cl.
*C07C 51/16* (2006.01)
(52) U.S. Cl.
USPC ........... 562/417; 562/405; 562/407; 562/409; 562/412
(58) Field of Classification Search
None
See application file for complete search history.

(56) References Cited

U.S. PATENT DOCUMENTS

| 3,845,117 | A | * | 10/1974 | Kollar ............................ 562/413 |
| 3,865,870 | A | | 2/1975 | Cronauer et al. ......... 260/524 R |
| 4,334,086 | A | | 6/1982 | Hanotier et al. .............. 562/413 |
| 4,465,633 | A | | 8/1984 | Goel et al. ................. 260/410.9 |
| 5,189,006 | A | | 2/1993 | Augustine et al. ............ 502/339 |
| 5,280,001 | A | | 1/1994 | Tso et al. ...................... 502/170 |
| 5,864,051 | A | * | 1/1999 | Iwasawa et al. .............. 568/479 |
| 6,160,159 | A | | 12/2000 | Smith ............................. 560/77 |
| 6,160,170 | A | * | 12/2000 | Codignola .................... 562/413 |
| 6,391,821 | B1 | * | 5/2002 | Satoh et al. ................... 502/300 |
| 6,528,683 | B1 | | 3/2003 | Heidemann et al. |

FOREIGN PATENT DOCUMENTS

| DE | 19630832 | 2/1998 |
| DE | 19745902 | 4/1999 |
| DE | 102004002262 | 8/2005 |
| EP | 0965383 | 12/1999 |
| EP | 1113238 | 7/2001 |
| WO | WO 97/17318 | 5/1997 |
| WO | WO 99/62857 | 12/1999 |
| WO | WO 02103693 | 12/2002 |
| WO | WO 2005066107 | 7/2005 |
| WO | WO 2007133973 | 11/2007 |
| WO | WO 2007133976 | 11/2007 |
| WO | WO 2007133978 | 11/2007 |

OTHER PUBLICATIONS

Benazzi et al.—Heterogeneous Catalyzed Benzylic Acetoxylation of Methylated Aromatic Hydrocarbons, Journal of Catalysis 140 pp. 311-327 (1993).
Benazzi et al.—Palladium-Catalyzed Benzylic Acetoxylation of Toluene, Journal of Molecular Catalysis 69, pp. 299-321 (1991).
Partenheimer—Methodology and Scopeof Metal/Bromide Autoxidation of Hydrocarbons, Elsevier pp. 69-158 (1995).
Yang, Advances In The Catalytic Systems for Synthesis of Terephthalic Acid via Oxidation of Paraxylene, Industrial Catalysis, vol. 12, No. 6, Jun. 2004, pp. 28-29.

* cited by examiner

*Primary Examiner* — Sudhakar Katakam
(74) *Attorney, Agent, or Firm* — Stephen L. Hensley

(57) ABSTRACT

Catalytic compositions for conversion of substituted aromatic feed materials to oxidized products comprising aromatic carboxylic acid derivatives of the substituted aromatic feed materials comprise solid particles comprising palladium in combination with at least one of antimony, bismuth and gold, and optionally, an additional metal or metalloid component effective to promote activity or selectivity of the palladium and antimony, bismuth or gold for oxidation to aromatic carboxylic acids. A process for oxidizing substituted aromatic feed materials comprises contacting the feed material with oxygen in the presence of such catalytic compositions in a liquid reaction mixture.

18 Claims, No Drawings

US 8,624,055 B2

PROCESS AND CATALYST FOR OXIDIZING AROMATIC COMPOUNDS

FIELD OF THE INVENTION

This invention relates to a catalyst composition and process for converting substituted aromatic compounds to oxidized products comprising aromatic carboxylic acids. More particularly, the invention relates to catalytic oxidation of feedstock materials comprising aromatic hydrocarbons having oxidizable substituent groups to an oxidized product comprising aromatic carboxylic acid using a catalyst composition that is active for such oxidation in the absence of bromine and comprises palladium and at least one of antimony, bismuth and gold, wherein particles disposed on a surface of the catalyst comprise at least a portion of the palladium in combination with at least a portion of at least one of antimony, bismuth or gold.

BACKGROUND OF THE INVENTION

Terephthalic acid and other aromatic carboxylic acids are widely used in the manufacture of polyesters, commonly by reaction with one or more glycols, and particularly ethylene glycol and combinations thereof with one or more higher homologues of alkylene glycols, for conversion to fiber, film, containers, bottles and other packaging materials, and molded articles.

In commercial practice, aromatic carboxylic acids are commonly made by liquid phase oxidation in an aqueous acetic acid solvent of methyl-substituted benzene and naphthalene feedstocks, in which the positions of the methyl substituents correspond to the positions of carboxyl groups in the desired aromatic carboxylic acid product. Oxidation is conducted by contacting the feedstock with air or another source of oxygen, which is normally gaseous, in the presence of a catalyst comprising cobalt and manganese promoted with a source of reactive bromine. The oxidation is exothermic and yields aromatic carboxylic acid together with by-products, including partial or intermediate oxidation products of the aromatic feedstock as well as oxidation and other reaction products of the acetic acid solvent such as methanol, methyl acetate, methyl bromide, carbon monoxide and carbon dioxide. Water is also generated as a by-product. The aromatic carboxylic acid oxidation product, by-products and intermediate oxidation products of the feedstock are commonly formed dissolved or as solids suspended in the liquid phase reaction mixture and are recovered by crystallization and solid-liquid separation techniques.

Pure forms of aromatic carboxylic acids are often favored for manufacture of polyesters for important applications, such as fibers, bottles, and other containers and packaging materials, because impurities, such as by-products generated from aromatic feedstocks, cause or correlate with color formation in polyesters made from the carboxylic acids and, in turn, off-color in polyester converted products. Aromatic carboxylic acids with reduced levels of impurities can be made by further oxidizing crude products from liquid phase oxidation, for example at one or more progressively lower temperatures and/or oxygen levels or during crystallization steps used to recover products of the oxidation, to convert partial oxidation products to the desired acid product. Preferred pure forms of terephthalic acid and other aromatic carboxylic acids with lower impurities contents are made by catalytically hydrogenating less pure forms of the acids in solution at elevated temperature and pressure using a noble metal catalyst. In commercial operations, liquid phase oxidation of alkyl aromatic feed materials to crude aromatic carboxylic acid and purification of the crude product are often conducted in continuous integrated processes in which a starting material for purification comprises crude product from oxidation.

A difficulty in manufacture of aromatic carboxylic acids results from use of bromine-promoted oxidation catalysts. Bromine sources used with the catalyst and reaction products thereof formed during oxidation are corrosive. Consequently, process equipment, such as oxidation reactors and off-gas treatment equipment, is normally constructed from titanium or other expensive, corrosion-resistant metals or alloys. In addition, process off-gas treatments to avoid atmospheric emissions of volatile bromine compounds, such as thermal or catalytic oxidation to convert organic bromine compounds to carbon oxides and molecular bromine with reduction of the latter to anionic bromine using sodium formate, add complexity and cost to manufacturing processes.

Eliminating bromine from cobalt-manganese oxidation catalysts is not practical for commercial scale aromatic carboxylic acid manufacture because yields of desired products are unacceptably low. Oxidation of acetic acid reaction solvent also tends to increase in cobalt and manganese-catalyzed oxidations without bromine. Sacrificial promoters, such as methyl ethyl ketone and acetaldehyde, have been proposed as alternatives to bromine but they are consumed in oxidation, thereby adding costs for their replacement and diverting oxygen from desired reactions. Sacrificial promoters can also negatively affect product quality in higher temperature oxidations. N-hydroxyphthalamide has been reported as a bromine-free promoter for cobalt-catalyzed reactions but lacks practical utility due to low solubility in acetic acid and conversion by multiple competing decomposition reactions to undesirable by-products.

Noble metal-catalysts for oxidizing methylated benzenes are proposed in U.S. Pat. No. 3,865,870 but conversions and selectivities to aromatic carboxylic acids are low and carbon oxides generation is high. Selective oxidation of alkanes and alkenes to aldehydes and ketones using catalysts containing noble metal particles dispersed on antimony oxide and having 1-30 mole % of the particles in the form of a noble metal-antimony alloy is proposed in U.S. Pat. No. 5,864,051 but there is no mention that the catalysts have any use for making carboxylic acids of for oxidation of aromatic compounds. Acetoxylation of substituted aromatic compounds by reaction with aliphatic monocarboxylic acids and oxygen using noble metal catalysts can yield benzylic alcohols and their esters with the monocarboxylic acids but with conversion does not proceed beyond the benzylic alcohols to more fully oxidized derivatives.

SUMMARY OF THE INVENTION

This invention provides a process and catalyst composition for conversion of feed materials comprising aromatic hydrocarbons having oxidizable substituent groups to an oxidized aromatic product and with selectivity to aromatic carboxylic acids. Unlike conventional commercial catalysts and processes for making aromatic carboxylic acids such as terephthalic and isophthalic acids, the invented process and catalyst are effective in the substantial or complete absence of bromine sources. While the process and catalyst are tolerant of bromine in some amounts, the presence of bromine in amounts commonly used in conventional processes adversely affects the invented process and catalysts, either reducing conversion to oxidized product or shifting selectivity from aromatic carboxylic acid products to less fully oxidized species. Surprisingly, aromatic carboxylic acid yields according to the invention exceed those achieved with known bromine-free catalyst systems and oxidations proceed beyond benzylic alcohols and without esterification thereof. The invention also provides surprising process benefits, including good yields and selectivities, in embodiments using water as a liquid medium for the reaction. Embodiments of the invention also can provide for oxidations to desired products with low levels of carbon oxides generation due to burning of aromatic feedstock and organic reaction solvents when used. In some embodiments, water generated as a by-product in the invented process can serve as a liquid reaction medium for the process, with desirable conversion and selectivities but insubstantial carbon oxides formation, thereby eliminating need for reaction solvents and addition of make-up liquid from external sources. The invention can provide improvements and advantages over compositions and processes according to commonly assigned International Applications PCT/US2007/068274, PCT/US2007/068268 and PCT/US2007/068261, filed May 4, 2007, which are incorporated herein by reference, related to catalyst compositions containing two or more metal or metalloid components, including palladium, antimony and bismuth, which are active, in the absence of bromine, for carboxylic acid-selective oxidation of aromatic compounds.

One embodiment of the invention provides a catalytic composition having activity for conversion of aromatic hydrocarbons substituted with oxidizable substituent groups in contact with oxygen in a liquid reaction mixture free of reactive bromine to oxidized aromatic product comprising aromatic carboxylic acid. The catalytic composition comprises palladium, and antimony or bismuth or gold or a combination thereof, wherein particles disposed on a surface of the catalyst comprise at least a portion of the palladium in combination with at least a portion of at least one of antimony, bismuth or gold. In other embodiments of the invention, catalysts additionally comprise an oxide or oxidizable form of at least one metal or metalloid which is effective to promote activity of palladium and antimony, bismuth or gold for oxidation of substituted aromatic hydrocarbons to aromatic carboxylic acid.

As used herein, "conversion of substituted aromatic compounds" refers to conversion of the compounds to oxidized aromatic derivatives and accordingly, expressions such as "oxidized aromatic derivatives" and "oxidized aromatic product" will be understood not to include carbon monoxide or carbon dioxide generated due to burning of aromatic starting materials or oxidation products. "Selectivity to aromatic carboxylic acid" refers to the weight of oxidized aromatic derivative or derivatives substituted with at least one carboxylic acid group expressed as a percentage of the total weight of oxidized aromatic derivatives. Unless otherwise stated, Groups of the Periodic Table of the Elements referred to herein correspond to "New Notation" designations according to the Periodic Table of the Elements as in, for example, Handbook of Chemistry and Physics, 78th Edition, CRC Press, 1997. The terms "Group" and "Groups" in reference to elements, metals and metalloids will be understood to refer to the elements appearing in the corresponding column or columns of such a Periodic Table. The expression "ppmw" is an abbreviation for parts per million by weight. The expression "Pd—Sb/Bi/Au" refers collectively or indiscriminately to palladium and any one or more of antimony, bismuth, and gold, i.e., to any one or more of palladium and antimony; palladium and bismuth; palladium and gold; palladium, antimony and bismuth; palladium, antimony and gold; palladium, bismuth and gold; and palladium, antimony, bismuth and gold.

Another embodiment of the invention provides a catalyst composition comprising a solid component in which a plurality of sub-micron-sized solid particles comprising palladium combined with at least one of antimony, bismuth and gold are present on a surface of the catalyst. In preferred embodiments, the catalyst composition additionally comprises a component comprising an oxide or oxidizable form of at least one metal or metalloid which is effective to promote activity of palladium and at least one of antimony, bismuth and gold for oxidation of substituted aromatic hydrocarbons having oxidizable substituents to aromatic carboxylic acid. The catalysts are active for oxidation of substituted aromatic hydrocarbons with high conversions and selectivities to aromatic carboxylic acids in the absence of bromine.

In another aspect, the invention provides a process for making a catalytic composition which, in preferred forms, has activity for conversion of substituted aromatic hydrocarbons having oxidizable substituent groups in contact with oxygen in a liquid reaction mixture free of reactive bromine to an oxidized aromatic product comprising aromatic carboxylic acid. The process for making such a catalyst composition comprises contacting at least one solid, particulate support material, preferably in the absence of reactive bromine sources, with a solution or solutions of at least one soluble palladium salt, at least one soluble salt of antimony, bismuth, gold or a combination thereof, and, optionally, at least one soluble salt of at least one additional metal or metalloid component capable of promoting activity of palladium and antimony, bismuth or gold, wherein the support material is contacted concurrently with at least the palladium and antimony, bismuth or gold salt solution or solutions, or in steps such that contacting with the palladium salt solution precedes or is concurrent with contacting with the antimony, bismuth or gold salt solution or solutions or combination thereof and, if used, the solution of at least one additional metal or metalloid salt is contacted in a subsequent step. A preferred stepwise preparation comprises combining components comprising at least one palladium salt and at least one antimony, bismuth or gold salt or combination thereof and at least one solid particulate support material in a solvent for the palladium and antimony, bismuth or gold salts or combination thereof, and in the absence of additional promoting metal or metalloid component, to form a slurry, removing solvent from the slurry to form a solid residue and calcining the solid residue, and combining with at least one of the slurry, the solid residue or the calcined solid residue a solution of a salt of at least one metal or metalloid promoter for the palladium and antimony, bismuth or gold.

Another aspect of the invention provides a process for conversion of feed materials comprising substituted aromatic compounds to oxidized aromatic products with selectivity to aromatic carboxylic acids. According to embodiments of this aspect of the invention, a process for conversion of an aromatic feedstock comprising a substituted aromatic hydrocarbon having one or more oxidizable substituent groups comprises contacting the aromatic feedstock with oxygen in a liquid reaction mixture formed by combining components comprising the aromatic feedstock, oxygen and a catalyst composition comprising palladium and at least one of antimony, bismuth and gold, wherein particles dispersed on a surface of the catalyst comprise at least a portion of the palladium in combination with at least a portion of at least one of antimony, bismuth or gold, to convert the feedstock to product comprising an aromatic oxidation product comprising aromatic carboxylic acid. In other embodiments, the catalyst used in such a process additionally comprises an oxide or oxidizable form of at least one metal or metalloid that is effective to promote activity of palladium and antimony, bismuth or gold for oxidation of the substituted aromatic hydrocarbon to aromatic carboxylic acid. In such embodiments, the metal or metalloid oxide or oxidizable form thereof can be present in solid form or in solution in the liquid reaction mixture. Preferably, the catalyst composition is free of bromine and is contacted with the aromatic feedstock in the absence of bromine.

In other embodiments, a process for manufacture of aromatic carboxylic acid comprises contacting a feed material comprising at least one dialkylarene, partially oxidized dialkylarene derivative or combination thereof, with oxygen in a liquid reaction mixture formed by combining components comprising the feed material, an oxygen source and catalyst according to the invention's aspects and embodiments, and comprising water or water and monocarboxylic acid solvent for the feed material, at temperature and pressure effective to maintain a liquid phase reaction mixture, to convert dialkylarene, partially oxidized dialkylarene derivative or combination thereof to aromatic carboxylic acid.

The invention also provides aromatic carboxylic acid compositions, and especially terephthalic acid, isophthalic acid and naphthalene dicarboxylic acid compositions. In some embodiments, the invention provides aromatic carboxylic acids prepared according to processes of the invention or using catalyst compositions according to the invention. Compositions according to other embodiments comprise terephthalic acid, isophthalic acid or naphthalene dicarboxylic acid, respectively, and, by weight thereof, about 0.001 to about 2000 ppmw palladium and about 0.001 to about 2000 ppmw antimony, bismuth, gold or a combination thereof, preferably wherein palladium and at least one of antimony, bismuth and gold are present in particles and more preferably in which an atom ratio of palladium to antimony, bismuth, gold or combination thereof is about 0.1:1 to about 10:1. In more specific embodiments, palladium and antimony, gold or bismuth are present in such compositions in the form of an alloy or mixed oxides or other combination thereof. In other embodiments, such compositions additionally include about 0.001 to about 500 ppmw of at least one additional metal or metalloid component, calculated as the element(s). In another embodiment, a terephthalic acid composition suitable for direct conversion by reaction with at least one glycol to polyester suitable for manufacture of fiber comprises terephthalic acid and, by weight thereof, about 0.001 to about 100 ppmw palladium, calculated as the element and about 0.001 to about 100 ppmw antimony, bismuth, gold or combination thereof, calculated as element(s), and preferably combined in the particles. In another embodiment, such compositions additionally comprise about 0.001 to about 100 ppmw of at least one additional metal or metalloid, calculated as element(s).

DETAILED DESCRIPTION OF THE INVENTION

Catalyst compositions according to aspects and embodiments of the invention comprise palladium, at least one of antimony, bismuth and gold wherein the catalyst comprises a solid having a surface with particles comprising palladium and at least one of antimony, bismuth and gold dispersed thereon. In addition to the particles comprising palladium and one or more of antimony, bismuth and gold, the compositions preferably comprise a metal or metalloid component, which can be present in or separate from the particles comprising palladium and antimony, bismuth, gold or combination thereof, and is an oxide or species convertible to oxide and promotes conversion or selectivity of palladium and antimony, bismuth or gold for oxidation of aromatic hydrocarbons substituted with oxidizable substituents to aromatic carboxylic acids. The expression "metal or metalloid" is used herein to refer collectively or indiscriminately to metallic elements as well as semi-metallic and other elements not considered metals in a strict sense but having metal-like properties. In referring to metals and metalloids and components of the catalyst composition, it will be understood that unless context indicates otherwise the terms are used in a broad sense to include the metals and metalloids as such as well as their compounds, complexes, alloys and combinations in other forms. Among elements that are or may be included in compositions according to aspects of the invention antimony, bismuth, tellurium, polonium, boron, aluminum, silicon and germanium are or may be considered metalloids. Significance of distinctions between metals and metalloids is not readily apparent for purposes of the invention.

The solid component of the invented catalysts is characterized by solid particles comprising palladium and one or more of antimony, bismuth and gold. The solid component can have such particles dispersed on the surface of a support material or it can be unsupported. The solid component itself may be, and preferably is, in the form of solid particles and it will be understood that in such cases surface particles of Pd—Sb/Bi/Au are present as discrete, sub-micron sized, smaller or subparticles of the overall solid particles. The presence and characteristics of Pd—Sb/Bi/Au surface particles can be determined using electronic imaging techniques such as scanning electron microscopy ("SEM"), transmission electron microscopy ("TEM") and scanning transmission electron microscopy ("STEM"). Presence and proportions of palladium, antimony, bismuth and gold in surface particles is determined by energy dispersive spectroscopic ("EDS") analysis of images generated by such techniques.

At least a portion of the total palladium content of the invented catalysts, and at least a portion of the total antimony, bismuth or gold content of the catalysts are present in combination in the form of such particles. In preferred forms of the invented catalysts, a majority or at least 50 weight %, and more preferably at least about 60 weight %, if not all or substantially all, of the palladium of the catalyst is present in the form of such particles. In preferred supported forms of the invented catalysts, at least about 60 wt % or at least about 70 wt % of the total palladium content of the catalyst, and more preferably at least about 90 wt % or 95 wt %, is present combined with at least one of antimony, bismuth and gold, and most preferably at least antimony, in surface particles. In other embodiments, however, particles comprising palladium combined with antimony, bismuth or gold can account for less of the overall palladium content. Antimony, bismuth and gold content of such particles may also account for such large proportions of total content of those species in the catalysts but may also be present in lower levels such as about 10 wt % or about 5 to about 8 wt %. The form or forms in which palladium, antimony, bismuth and gold not combined in surface Pd—Sb/Bi/Au particles may be present does not appear to be critical and can include oxides, elemental metal or metalloid forms and other forms.

Proportions of total palladium and antimony, bismuth, gold or combination thereof in the invented catalytic compositions can vary widely. Preferably, palladium and one or more of antimony, bismuth and gold are present in amounts such that the atom ratio of palladium, to antimony, bismuth, gold or combination thereof is about 1:1000 to about 1000:1, and more preferably about 1:100 to about 100:1. In more specific embodiments, compositions comprising surface particles in which palladium and at least one of antimony, bismuth and gold are present in ratios of about 0.1 to about 10 atoms palladium to 1 atom antimony, bismuth, gold or combination thereof, and more preferably about 0.5:1 to about 10:1, as determined by EDS from SEM images (TEM and STEM images also can be used), provide compositions with high oxidation activity and selectivity to products in which oxidizable substituents of substituted aromatic feedstocks are fully oxidized to aromatic carboxylic acid groups. More preferably, surface particles of the catalysts comprise palladium and one or more of antimony, bismuth and gold in an atom ratio of about 0.5:1 to about 5:1. Other things being equal, palladium-antimony combinations in the surface particles tend to provide better reactivities and selectivities than combinations of palladium and bismuth or palladium and gold. When using combinations in which palladium is present with antimony and one or both of gold and bismuth in the surface particles, antimony most preferably is present in greater proportion than bismuth and gold. In a particular embodiment, compositions according to the invention have surface particles comprising palladium, antimony and bismuth or gold in combination in atom ratios of about 0.5-5:1:0.5.

Precise chemical identities of palladium and antimony, bismuth, gold or combinations thereof as they exist in the surface particles of the invented compositions are not fully known. Palladium and one or more of antimony, bismuth and gold are present in the particles in combined form based on TEM and SEM analyses of fresh and used catalyst samples exhibiting good oxidation activities and carboxylic acid selectivities. Particles comprising Pd—Sb/Bi/Au may be present in the form of alloys, mixed metal oxides and other combined forms and in combinations of different forms. In some embodiments, presence of palladium and antimony in a single, homogeneous phase in such particles has been observed, indicating presence of a palladium-antimony alloy; however, such analyses do not exclude the presence of combinations in other forms. Uncombined palladium metal in surface particles comprising Pd—Sb/Bi/Au preferably accounts for less than half, more preferably less than about 40 wt % or less than about 30 wt % and most preferably no more than 10 wt %, of the particles. In catalysts in which surface particles comprising palladium alloyed with antimony, bismuth or gold are present, palladium present in the particles is predominantly in alloy form. At least 50% of the palladium in such alloy-containing particles, and more preferably about 60 to 100%, is present alloyed with antimony, bismuth or gold. A preferred catalyst comprises Pd—Sb/Bi/Au surface particles comprising palladium-antimony, palladium-bismuth, palladium-gold, palladium-antimony-gold or palladium-antimony-bismuth alloys and, in some embodiments, those having antimony present, optionally with bismuth, gold or both. Preferred palladium to antimony atom ratios are about 1:1 to about 3:1.

In embodiments in which the invented catalysts additionally comprise at least one promoting metal or metalloid in oxide or oxidizable form, presence of the promoting metal or metalloid component in the sub-micron Pd—Sb/Bi/Au particles has not been observed consistently in microanalyses although presence thereof does not appear to significantly affect catalyst performance. Accordingly, while preferred catalysts include such promoting metal or metalloid components, presence of such components in Pd—Sb/Bi/Au surface particles is not critical.

Preferred catalysts according to the invention comprise sub-micron size Pd—Sb/Bi/Au particles disposed on surfaces of the invented catalysts, with particle diameters determined by TEM of less than 1000 nm. In supported catalysts according to the invention, TEM/STEM analyses have shown particles dispersed over surfaces of the support as discrete particles or clusters thereof. Larger agglomerates of particles are also observed. In some embodiments, analyses of randomly selected surface particles comprising palladium and one or more of antimony, bismuth and gold have shown the presence of particles with average particle diameters in the range of about 1 to 500 nanometers ("nm"), and preferably about 1 to about 200 nm, with averages of about 1 to about 20 nm or 2 to 15 nm or 3 to 10 nm being more preferred.

Preferred catalyst compositions according to embodiments of the invention include, in addition to palladium and at least one of antimony, bismuth and gold wherein at least a portion of the palladium and at least a portion of at least one of the antimony, bismuth and gold are present in combination in particles dispersed on a catalyst surface, at least one additional metal or metalloid component which is present as one or more oxide or oxidizable form. As described above, uncombined palladium and antimony, bismuth or gold may be present as oxides or other oxidizable forms in other embodiments of the invented catalysts and it will be understood that the "additional metal or metalloid component" according to this preferred embodiment refers to a metal or metalloid component comprising at least one metal or metalloid that is not the palladium, antimony, bismuth or gold. The additional metal or metalloid component according to this embodiment functions as a promoter or activator for palladium and antimony, bismuth or gold in the sense that yields of aromatic carboxylic acids produced by oxidation of substituted aromatic hydrocarbons with oxidizable substituents in the presence of the palladium and antimony, bismuth or gold of the catalysts are greater in the presence of the additional metal or metalloid component than in the absence of such a component. A preferred additional metal or metalloid component for carboxylic acid-selective oxidation of substituted aromatic hydrocarbons is molybdenum. Other suitable metals and metalloids include titanium, zirconium, vanadium, niobium, tantalum, chromium, tungsten, germanium, tin, lead, aluminum, calcium, cadmium, cerium, copper, iron, gallium, indium, iridium, potassium, lithium, sodium, rhodium, ruthenium and zinc, and especially the Group 4, 5 and 6 metals and metalloids and, more particularly, titanium, vanadium, chromium, niobium, and combinations thereof.

When present in the invented catalysts in solid form, including unsupported forms and forms supported either separately from or with supported Pd—Sb/Bi/Au particles, the promoting, additional metal or metalloid component is commonly present as oxide although metal or metalloid and other oxidizable forms may be present.

For use in oxidation of substituted aromatic hydrocarbons to aromatic carboxylic acids, the additional metal or metalloid component also can be used in forms that are soluble in the liquid oxidation reaction mixture, such as various salts or salt solutions. Accordingly, in oxidation processes conducted in the presence of water, aqueous monocarboxylic acid reaction solvents or other liquid reaction media, the invention includes use of catalysts in heterogeneous form as well as hybrid forms in which the catalyst includes a heterogeneous component comprising palladium combined with antimony, bismuth, gold or combinations thereof in the form of solid particles on the catalyst surface and a soluble, homogeneous oxide or oxidizable form of the metal or metalloid promoter.

As with palladium, antimony, bismuth and gold, promoting metal or metalloid component content of the invented catalysts according to this embodiment can vary. Palladium to promoting metal or metalloid atom ratios preferably are about 1:1000 to about 1000:1 and more preferably about 1:100 to about 100:1. In catalysts comprising molybdenum as an additional metal component, palladium to molybdenum atom ratios preferably are about 100:1 to about 1:100, more preferably about 1:10 to about 10:1 and still more preferably about 0.3:1 to about 5:1. Proportions of metal and metalloid elements in various combinations can be determined and optimized for particular combinations and usages by persons skilled in catalytic oxidations for manufacture of aromatic carboxylic acids guided by the description and examples appearing herein.

In one embodiment, a form of the invented catalytic compositions comprises a water and/or monocarboxylic acid-insoluble composition formed from palladium and antimony, bismuth, gold or a combination thereof, optionally also including an additional promoting metal or metalloid component in oxide or oxidizable form. Such insoluble compositions are conveniently prepared by contacting a solution or solutions of individual or combined metal and metalloid salts such that palladium and antimony, bismuth, gold or their combination are contacted prior to or simultaneous with addition of a solution comprising the optional additional promoting metal or metalloid. In one embodiment, a solid catalyst composition is conveniently prepared by contacting a solution of at least one palladium(II) salt and at least one antimony (III), bismuth(III) or gold(III) salt with air or another oxygen source at above-ambient temperatures, such as about 80° C. or greater and preferably about 90° C. to about 150° C., and, if a promoting metal or metalloid component is included, contacting the result with a solution comprising at least one soluble salt of the promoting metal or metalloid.

In another embodiment, a preferred form of the invented catalyst compositions comprises a solid component having particles comprising palladium in combination with at least one of antimony, bismuth and gold carried on a solid support material in the form of a supported composition. Preferred supported catalyst compositions have a plurality of discrete particles comprising palladium and antimony, and optionally also one or both of bismuth and gold, dispersed or clustered on the support surface. In embodiments of the invention in which the catalyst comprises an additional promoting metal or metalloid component, it may be present on such a support, separately supported or present in other forms. When carried together with the Pd—Sb/Bi/Au particles on a support, the additional promoting metal or metalloid component preferably is present in forms ranging from individual atoms or oxide molecules to crystallites or small particles of metal or metalloid oxide. In some embodiments, metal or metalloid oxide promoter particles present on catalyst surfaces that also include sub-micron Pd—Sb/Bi/Au particles have average particle sizes of about 0.5 to about 20 nm or about 0.5 to about 5 nm or about 1 to about 3 nm. In preferred embodiments, compositions in which promoting metal or metalloid particles present on support or catalyst surfaces that also carry Pd—Sb/Bi/Au particles comprise a plurality of the promoting metal or metalloid component particles disposed in close proximity to Pd—Sb/Bi/Au particles. Microanalyses of supported catalysts comprising surface-disposed promoting metal or metalloid component particles and Pd—Sb/Bi/Au particles indicate that promoting metal or metalloid particles exposed to electron beams used for imaging can exhibit mobility on support surfaces.

Supported catalyst components and compositions according to the invention comprise support materials in the form of solid particulates, such as powder, particles, pellets, granules, spheres (including microspheres), porous particles, nanotubes, colloidal and non-colloidal powders and the like. Suitable support materials include carbon, silicon carbide and refractory metal oxides such as silica, alumina, cerium oxide, silica-alumina, titania and zirconia. Preferred supports for compositions used in oxidations according to the invention are materials that are stable in the sense of maintaining physical integrity and metal or metal and metalloid loadings suitable to process operation over prolonged exposures to process conditions and use. Substantial insolubility of the support and resistance to significant loss of catalyst metal or metalloid loadings in water or aqueous acetic acid solutions at temperatures of at least about 100° C. for a period on the order of several days, for example at least 7 days, are indicative of suitable support materials. Preferred supports for catalysts used in oxidation of substituted aromatic hydrocarbons and partially oxidized derivatives thereof include carbons and non-zeolitic metal oxides such as alpha alumina, silicas, cerium oxide and titania, including rutile and anatase forms thereof and forms in which both anatase and rutile phases are present. Non-zeolitic supports are preferred for oxidation processes according to the invention due to their greater stabilities under process conditions. Other supports which may be suitable include high strength, acid stable silicon carbides, zirconia, gamma alumina and zinc oxide. Examples of commercially available carbon supports have BET surface areas of about one or even a fractional square meter per gram up to about 1500 $m^2/g$. Metal oxide surface areas tend to range from about 1 $m^2/g$ in the case of rutile titanias up to about 500 $m^2/g$ for silicas. Catalyst metal and metalloid loadings of supported compositions are not critical though loadings in the range of about 0.1, and preferably 0.5 to about 20 and preferably 15 wt % of the supported composition are preferred.

Supported compositions comprising surface particles that comprise palladium combined with one or more of antimony, bismuth and gold can be prepared by contacting solid support materials, preferably in the form of powder, pellets, granules, extrudates, porous particles or other particulate solid form suited to process use, with one or more solution or solutions of catalyst metal compounds in water or another solvent that is inert to the support and easily removed, after which the solvent is removed, such as by drying at ambient or elevated temperature. For such preparations, a single solution of all catalyst metal or metalloid salts or compounds can be employed as can concurrent or sequential impregnations using solutions of individual catalyst metals or metalloids or combinations. Palladium and antimony, bismuth or gold salt solutions preferably are contacted with a support in combination or in steps with palladium preceding the antimony, bismuth, gold or combinations thereof. When a single support material is impregnated with palladium, one or more of antimony, bismuth and gold, and promoting metal or metalloid, the promoting metal or metalloid salt solution preferably is contacted concurrently with palladium and antimony, bismuth or gold salt solutions or in a separate step subsequent to concurrent or stepwise impregnations with palladium and antimony, bismuth or gold. In sequential impregnations, palladium salt solution is preferably contacted with the support prior to contacting with the antimony, bismuth or gold salt solutions and also prior to contacting with promoting metal or metalloid salt solution if used. Support materials pre-impregnated with supported palladium components can be contacted with a solution or solutions of antimony, bismuth or gold salts or a combination thereof and then with promoting metal or metalloid salt solutions if used. Contacting with single or combined salt solutions is preferably followed by evaporation of solvent.

Metal and metalloid salts used to prepare insoluble catalyst compositions or components in supported or unsupported form can be in any valence state that provides a composition having activity and selectivity under conditions of use for oxidation of substituted aromatic compounds in which substituent groups comprise an oxidizable alpha carbon to oxidized product comprising aromatic carboxylic acid derivatives of the substituted aromatic compound. Preferred salts are palladium(II), antimony(III), bismuth(III), gold(I) or (III) and molybdenum(II), (III), (IV) and (VI) salts. Suitable salts include acetates, oxalates, benzoates and other carboxylates, hydroxides, nitrates, ammonium salts, sulfates, sulfites, oxides, hydrides, carbonates, phosphates, methanesulfonates, acetylacetonates, methoxides, ethoxides, propoxides, butoxides and other alkoxides. Bromides and other halogen-containing salts can be used in preparing supported catalysts or components because solvent evaporation and calcination techniques commonly are effective to remove halogen residues that otherwise might impair catalyst or oxidation performance; however, halogenated salts are unnecessary and best avoided in preparing unsupported catalysts and catalyst components.

Any suitable solvent for the palladium, antimony, bismuth, gold and optional promoting metal or metalloid salts used in catalyst preparations can be employed for preparation of supported or unsupported forms of catalyst components and compositions. Preferred organic solvents are $C_{1-8}$ monocarboxylic acids and aqueous solutions thereof and especially acetic acid or aqueous acetic acid. Water is also a preferred solvent. Salt solutions can be dilute or concentrated and can include various additives such as solubilizing components for the metal salts, dispersants, nucleating agents, anti-agglomerates, reducing agents and the like.

Examples of suitable palladium compounds for preparing catalytic components or compositions include Pd(II) acetate, Pd(II) acetylacetonate, Pd(II) propionate, Pd(II) nitrate, Pd(II) cyanide, Pd(II) hydroxide, Pd(II) oxide, Pd(II) sulfate and Pd(II) sulfide. For preparing supported compositions, palladium, either alone or with antimony, bismuth, gold or a combination thereof, carried on a support such as described above and palladium(0) alloys also may be useful.

Examples of useful antimony, bismuth and gold compounds include Sb(III) acetate, Sb(III) butoxide, Sb(III) ethoxide, Sb(III) isopropoxide, Sb(III) methoxide, Sb(III) oxide, Sb(IV) oxide, Sb(V) oxide, Sb(III) propoxide, Sb(III) sulfide, Sb(V) sulfide, antimony tin oxide; bismuth salts such as Bi(III) acetate, Bi(III) carbonate, Bi(III) chloride, Bi(III) citrate, Bi(III) molybdate, Bi(III) nitrate, Bi(III) oxide, Bi(III) phosphate, Bi(III) salicylate, Bi(III) sulfide, Bi(III) titanate and Bi(III) triflate, Au(I) sulfide, Au(I) cyanide, Au(III) hydroxide, Au(III) oxide, and Au(III) sulfide.

Examples of other metal and metalloid salts include Ti(IV) butoxide, Ti(IV) carbide, Ti(IV) carbonitride, Ti(IV) diisopropoxide bis(acetylacetonate), Ti(IV) ethoxide, Ti(II) hydride, Ti(IV) isopropoxide, Ti(IV) methoxide, Ti(IV) nitrate, Ti(IV) nitride, Ti(IV) oxide, Ti(II) oxide acetylacetonate, Ti(IV) oxysulfate, Ti(IV) propoxide, Ti(III) sulfate and Ti(IV) sulfide; zirconium compounds such as Zr nitride, Zr(IV) oxide, Zr(IV) sulfate, Zr(IV) nitrate, Zr(IV) propoxide, Zr(IV) trifluoroacetylacetonate, Zr(IV) hydroxide, Zr(IV) ethoxide, Zr(II) hydride, Zr(IV) hydrogenphosphase; vanadium compounds such as V(III) acetylacetonate, V(IV) carbide, V(IV) oxide sulfate, V(V) oxytriethoxide, V(V) oxytriisopropoxide, V(V) oxytripropoxide, vanadium oxide acetylacetonate, vanadium oxide 2,3-naphthalocyanine; niobium compounds such as Nb(IV) carbide, Nb(V) ethoxide and Nb nitride; molybdenum compounds such as Mo(II) acetate, Mo(II) carbide, Mo(0) hexacarbonyl, Mo(VI) oxide, Mo(IV) sulfide, molybdic acid and various molybdates ($MoO_4^-$); chromium salts including Cr(III) acetate, Cr(III) acetylacetonate, Cr(III) carbide, Cr hexacarbonyl, Cr(III) nitrate, Cr(III) nitride, Cr(III) oxide, Cr(VI) oxide, Cr(III) phosphate, Cr(III) sulfate, and various chromates ($CrO_4^-$) and dichromates ($Cr_2O_7^{-2}$).

Other suitable salts include acetates, oxalates, benzoates and other carboxylates, hydroxides, nitrates, sulfates, sulfites, oxides, hydrides, carbonates, phosphates, methanesulfonates, acetylacetonates, methoxides, ethoxides, propoxides, butoxides and other alkoxides of promoting metals and metalloids that may be used alone or in combinations, such as aluminum, calcium, cadmium, cerium, copper, iron, gallium, indium, iridium, potassium, lithium, sodium, rhodium, ruthenium and zinc.

For preparation of supported catalyst components and compositions, so-called "incipient wetness techniques," in which a support is contacted with a solution of the catalyst metal or metalloid compound in an amount that just wets the support and then the resulting wetted support is dried, are known and well suited to manufacture of the catalysts. In another suitable technique, sometimes referred to as the "excess solution method," the support is contacted with a greater volume of one or more impregnation solutions than required to wet the support, after which solvent is removed by drying, for example by evaporation under ambient conditions or with moderate heating. Excess solution techniques are sometimes preferred over incipient wetness methods when using low surface area supports. Other techniques, such as spraying a solution of catalyst metal compound or compounds onto a support material also are suitable.

Post-treatments, such as heating and high temperature calcinations in the presence of air or nitrogen, and reduction with hydrogen, also may be yield catalyst compositions or components with advantages or characteristics of interest. Suitable calcination temperatures can vary somewhat depending on support compositions but preferably range from about 100 to about 600° C. and more preferably from about 200 to about 500° C. or 250 to about 400° C. Preferred catalysts according to the invention are prepared by sequential or simultaneous contacting of support materials with an aqueous solution or solutions of soluble palladium and antimony, bismuth or gold salts in aqueous solvent or solvents, followed by evaporation of solvent or solvents, calcination in the presence of oxygen at elevated temperature, preferably at about 200 to about 450° C., and, for catalysts in which additional promoting metal or metalloid component is carried on the same support, contacting the calcined solid with at least one aqueous solution comprising a promoting metal or metalloid salt and removing solvent from the result. More preferably, such compositions are calcined or calcined and reduced at elevated temperatures after solvent removal. Solubilizing aids, such as citric and other organic acids, are useful to aid in dissolving and dispersing palladium and antimony, bismuth or gold components in catalyst preparations.

Catalyst compositions according to the invention exhibit desirable activities for oxidation of substituted aromatic substrates with good selectivity to aromatic carboxylic acid derivatives. The catalysts are active and selective for such oxidations, commonly with low levels of carbon oxides generation, in the absence of reactive bromine sources. The mechanism or mechanisms by which the compositions catalyze reaction of oxidizable substituent-bearing aromatic compounds with oxygen to oxidized products with selectivity to aromatic carboxylic acids is not understood. Accordingly, it will be understood that the description of the invented catalytic compositions in terms of their constituent elements, characteristics and correlations with oxidation performance is not intended as limiting with respect to theory or mechanisms.

Activity and selectivity of catalyst compositions according to the invention in the absence of reactive bromine afford a number of benefits and opportunities for advantage over conventional processes for oxidizing aromatic substrates using bromine-promoted catalysts, as well as alternative proposals that rely on catalysts with low activities and selectivities, alkaline reaction media or catalysts prone to conversion to insoluble precipitates that can cause plugging in other process steps. In the manufacture of aromatic carboxylic acids from aromatic feed materials, and particularly alkyl aromatic hydrocarbons such as toluene, xylenes and methyl naphthalenes, the invention can provide opportunities for process simplification by allowing bromine to be eliminated from oxidation process and catalyst systems. Such opportunities include potential not only for eliminating or reducing requirements for treatment of process effluents to reduce or eliminate unwanted brominated by-products of the process, but also for simplifying metallurgy of reaction vessels, agitators and other equipment from titanium metal and nickel alloy steel solid and clad constructions to less corrosion resistant constructions such as stainless or mild steels or with reduced cladding. Furthermore, even higher temperature oxidations, for example at about 170° C. and greater, can be conducted without substantial burning of aromatic substrates or carboxylic acid solvents to carbon oxides. Oxidations in water or dilute aqueous organic acid liquid reaction media or solvents also provide opportunities for reduced organic solvent usage, reduced corrosivity of reaction mixtures, process streams, effluents and off-gases, and added potential to simplify processes, equipment and metallurgy.

Briefly, the invented process in its embodiments provides for conversion of an aromatic feedstock comprising a substituted aromatic hydrocarbon having oxidizable substituents to oxidized aromatic product comprising at least one aromatic carboxylic acid derivative of the substituted aromatic compound by contacting the aromatic feedstock with oxygen in a liquid reaction mixture in the presence of a catalytic composition according to the invention. Preferred substituted aromatic hydrocarbons are those in which at least one substituent group includes an oxidizable alpha carbon atom. In this context, an "alpha carbon atom" refers to a carbon atom linked directly to an aromatic ring and an "oxidizable alpha carbon atom" is an alpha carbon atom having at least one hydrogen bonded directly to it. Oxidation of substituted aromatic feed materials with oxidizable alpha carbon atom-containing substituents is selective to aromatic carboxylic acid derivatives in which at least one substituent group is a carboxylic acid group having an alpha carbon atom but the oxidation product can also include derivatives with less fully oxidized substituents or in which one but not all of the substituent groups of the starting material is oxidized to a carboxylic acid group while other groups are less fully oxidized or remain unconverted. Conversion to oxidized aromatic derivatives of aromatic starting materials preferably is at least about 65 mole %, and more preferably at least about 80 mole % and, in some embodiments of the invention, at least 90 or 95 mole %. Selectivity to aromatic carboxylic acid derivatives, taking into account all carboxylic acid-substituted oxidation products of the aromatic feed material, is preferably at least about 60% and more preferably at least 80% and still more preferably at least 90%. According to some embodiments of the invention, conversions of at least about 80 mole % with at least 80%, and more preferably 90% or greater, selectivity to a single aromatic acid derivative are achieved. In such embodiments, the invention provides processes for making such derivatives in which recovery techniques and recycle of intermediate oxidation products can be minimized or simplified. Preferred aromatic carboxylic acids for which embodiments of the invented process are suited are those manufactured in a liquid phase reaction system and include mono- and polycarboxylated species with one or more aromatic rings and in which at least one, and preferably all, carboxylic acid groups comprises carbon linked directly to the aromatic ring, i.e., an alpha carbon atom. Examples include terephthalic, isophthalic, trimesic, trimellitic, phthalic, benzoic and naphthalene dicarboxylic acids.

Liquid phase oxidation according to embodiments of the invented process is conducted at elevated temperature and pressure, and preferably under pressure effective to maintain a liquid phase reaction mixture. Oxidation of the aromatic feed material in the liquid phase oxidation step produces oxidized product comprising aromatic carboxylic acid as well as reaction by-products such as partial or intermediate oxidation products of the aromatic feed material. The liquid-phase oxidation and associated or other steps, such as product recoveries, separations, purifications and off-gas and liquid effluent treatments, can be conducted in batch or as continuous or semi-continuous processes.

Suitable aromatic feed materials for the oxidation generally comprise an aromatic hydrocarbon substituted at one or more positions, normally corresponding to positions of the carboxylic acid groups of the aromatic carboxylic acid being prepared, preferably with at least one group that includes an alpha carbon atom that is oxidizable to a carboxylic acid group. The oxidizable substituent or substituents can be alkyl groups, such as a methyl, ethyl or isopropyl, or groups already containing oxygen, such as formyl, acyl or hydroxyalkyl groups. Substituents can be the same or different. The aromatic ring of feedstock compounds can be a benzene nucleus or bi- or polycyclic, such as a naphthalene nucleus. The number of oxidizable substituents of the feedstock compound can equal the number of sites available on the aromatic ring, but is generally less, preferably 1 or 2, and most preferably 2. Examples of useful feed compounds, which can be used alone or in combinations, include toluene, ethylbenzene and other alkyl-substituted benzenes, o-xylene, p-xylene, m-xylene, tolualdehydes, toluic acids, alkyl benzyl alcohols, 1-formyl-4-methylbenzene, 1-hydroxymethyl-4-methylbenzene, methylacetophenone, 1,2,4-trimethylbenzene, 1-formyl-2,4-dimethylbenzene, 1,2,4,5-tetramethylbenzene, alkyl-, formyl-, acyl-, and hydroxylmethyl-substituted naphthalenes, such as 2,6-dimethylnaphthalene, 2,6-diethylnaphthalene, 2,7-dimethylnaph-thalene, 2,7-diethylnaphthalene, 2-formyl-6-methylnaphthalene, 2-acyl-6-methylnaphthalene, 2-methyl-6-ethylnaphthalene and partially oxidized derivatives of the foregoing.

For manufacture of aromatic carboxylic acids by oxidation of correspondingly substituted aromatic hydrocarbon precursors, e.g., manufacture of benzoic acid from mono-substituted benzenes, terephthalic acid from para-disubstituted benzenes, phthalic acid from ortho-disubstituted benzenes, and 2,6- or 2,7-naphthalenedicarboxylic acids from, respectively, 2,6- and 2,7-disubstituted naphthalenes, it is preferred to use relatively pure feed materials, and more preferably, feed materials in which content of the precursor corresponding to the desired acid is at least about 95 wt. %, and more preferably at least 98 wt. % or even higher. Preferred precursors include alkyl aromatic compounds as well as their partially oxidized derivatives. By way of example, in the case of para-xylene, examples of partially oxidized derivatives that also can be converted to more fully oxidized product comprising aromatic carboxylic acid include p-methylacetophenone, p-toluic acid, p-hydroxymethyl benzoic acid, tolualdehyde and 4-carboxybenzaldehyde. A preferred aromatic hydrocarbon feed for terephthalic acid comprises para-xylene. A preferred feed material for benzoic acid comprises toluene.

Oxidation of aromatic feed materials according to the invented process is conducted in a liquid reaction mixture. Water can be used as the reaction medium with surprising conversions and selectivities to aromatic carboxylic acid products. Water generated as by-product in oxidations of aromatic feed materials according to the invention can serve as liquid medium for the reaction, thereby eliminating or reducing the need for addition of water to the process from external sources or by recycle of water from other process steps and also eliminating use or presence of different liquids and process and equipment complexities that may be needed for their separation and recycle or re-use. In one embodiment, a preferred liquid medium for the reaction mixture comprises water and not more than about 10 wt % $C_1$-$C_8$ monocarboxylic acid. When used, preferred solvents for aromatic feed materials in the liquid phase reaction comprise low molecular weight monocarboxylic acids and preferably a $C_1$-$C_8$ monocarboxylic acid, for example acetic acid, propionic acid, butyric acid, valeric acid and benzoic acid. Acetic acid is a preferred monocarboxylic acids. Solvents in the form of aqueous solutions, for example about 40 to about 95 wt. % solutions of the acid can be used with good results. Ethanol and other co-solvent materials that oxidize to monocarboxylic acids under liquid phase oxidation reaction conditions also can be used as is or in combination with monocarboxylic acids. While water is a preferred liquid medium for the process and monocarboxylic acid solvents for the liquid reaction medium are preferred, other suitable solvents or liquid media can be used. According to preferred embodiments of the invention in which the process is conducted in a non-alkaline reaction mixture, examples of liquid media that can be used with or as alternatives to water and $C_1$-$C_8$ monocarboxylic acids, include oxalic acid, malonic acid, methyl malonic acid, dimethyl malonic acid, succinic acid, methyl succinic acid, glutaric acid and cyanoalkanes or cyanoarenes, for example, acetonitrile or benzonitrile, respectively, and including aqueous forms thereof and combinations of two or more thereof may be suitable.

In preferred embodiments, liquid phase oxidation according to the invention is carried out in the absence or substantial absence of reactive bromine. Preferably reactive bromine is present at levels less than about 2 wt % based on catalyst metal and metalloid weight. In preferred processes according to the invention, reactive bromine content of the liquid oxidation reaction mixture is no more than about 50 ppm by weight of the reaction medium. Minor amounts of reactive bromine that do not have substantial adverse affects on catalyst performance may be tolerated but the reaction system most preferably is free of reactive bromine as it is unnecessary, corrosive and forms corrosive by-products.

Reactants for the liquid phase oxidations according to the invention include a source of molecular oxygen. Gaseous oxygen sources are preferred, with air conveniently used as such a source. Oxygen-enriched air, pure oxygen and other gaseous mixtures comprising molecular oxygen also are useful.

Proportions of aromatic feed material, catalyst, oxygen and liquid reaction medium or solvent are not critical and can be varied widely based on factors that include choice of reactants, liquid medium or solvent and catalyst compositions and intended oxidized and aromatic carboxylic acid products, details of process design and operating factors. Solvent or liquid reaction medium to aromatic feedstock weight ratios ranging from about 1:1 to about 30:1 are preferred, with about 2:1 to about 5:1 being more preferred although higher and lower ratios, even in the range of hundreds to one also can be used. Oxygen typically is used in at least a stoichiometric amount based on aromatic feed material but, in the case of gaseous oxygen, not so great, taking into account reactant and solvent compositions, reaction conditions and rates, that off-gases generated as a result of the liquid phase oxidation form a flammable mixture. Oxygen, commonly in the form of air, is preferably supplied at a rate effective to provide at least about 3 to about 5.6 moles molecular oxygen per mole of aromatic hydrocarbon feed material. Catalyst is used in amounts effective for conversion of aromatic feed material to oxidized product and can vary. Other things being equal, reaction rates and consumption of oxygen in oxidations using the invented catalysts increase with increasing catalyst concentrations in the oxidation reaction mixture. In batch and continuous slurry processes, the invented catalytic compositions preferably are used in amounts such that concentrations of total catalyst metals and metalloids, based on weight of liquid medium or solvent used in oxidation, are at least about 100 ppmw, and more preferably at least about 500 ppmw, up to about 10,000 ppmw, more preferably up to about 6,000 ppmw, and still more preferably up to about 3,000 ppmw. In continuous flow processes such as fixed, fluid and ebullated bed processes, weight hourly space velocities of substituted aromatic hydrocarbon feed per weight of catalyst composition can be determined by routine experimentation based on the batch and semi-continuous oxidation trials and results according to the Examples appearing herein.

Liquid phase reactions for oxidation of aromatic feed material to oxidized products comprising one or more carboxylic acid-substituted aromatic derivatives are conducted in a suitable oxidation reaction zone, which normally comprises one or more reaction vessels. Suitable reaction vessels are configured and constructed to withstand the high temperature and pressure conditions and generally acidic liquid phase reaction mixture present in the reaction zone and to provide for addition and mixing of catalyst, liquid and gaseous reactants and reaction media or solvent and removal of oxidized product or a liquid effluent comprising such product for recovery thereof. Oxidations according to the invention in some of its embodiments tend to be exothermic. Heat of reaction can conveniently be controlled by evaporating a reaction off-gas from the liquid reaction mixture and removing the off-gas from the reaction zone. In such cases, the reaction vessel also should be configured for venting of off-gas. Reactor types which can be used include slurry, continuous stirred tank reactors, bubble column reactors, tubular reactors, ebullating bed, fixed or packed bed and trickle bed reactors. A preferred form of stirred tank reactor is a columnar vessel, normally with a central axis extending vertically when the vessel is positioned for use and having one or more mixing features for mixing reactants, including distributing gaseous reactants or reactant sources, if used, within a liquid phase, typically boiling reaction mixture. Typically, the mixing feature comprises one or more impellers mounted on a rotatable or otherwise movable shaft. For example, impellers may extend from a rotatable central vertical shaft. Reactors may be constructed of materials designed to withstand the particular temperatures, pressures and reaction compounds used. Fixed, fluidized and ebullated bed reactors and slurry reactors are preferred. Stainless or duplex steels are preferred materials of construction for oxidations conducted without sources of reactive bromine although more corrosion-resistant metals or alloys, such as titanium or high nickel steel alloys can be used if desired.

A reaction mixture for the liquid phase oxidation is formed by combining components comprising aromatic feed material, liquid reaction medium or solvent and the catalytic composition according to the invention or components thereof and adding a suitable oxygen source to the mixture. In continuous or semi-continuous processes, components can be combined in one or more mixing vessels before being introduced to the oxidation zone; however, the reaction mixture can also be formed in the oxidation zone. As noted above, in oxidations using water as liquid medium for the reaction mixture, water generated as by-product of the oxidation can serve as the liquid media.

Contacting aromatic feed material with oxygen in the presence of catalytic composition according to the invention is conducted under reaction conditions effective for conversion of substituted aromatic compounds having oxidizable substituents to oxidized product comprising aromatic carboxylic acid derivatives of the substituted aromatic feed materials. Preferred reaction conditions include temperatures and pressures effective for such conversion while maintaining a liquid phase reaction mixture. Temperatures of about 100 to about 300° C. are preferred. Preferred temperatures are about 140° C., and more preferably about 160° C., to about 230° C., and more preferably about 200° C. Pressure of the liquid phase reaction mixture can be used to control the temperature at which the liquid phase reaction mixture boils and is preferably selected to maintain a substantial liquid phase reaction mixture. Pressures of about 5 to about 40 kg/cm$^2$ gauge are preferred, with preferred pressures for particular processes varying with feed and solvent or liquid reaction media compositions, temperatures and other factors and more preferably ranging between about 10 to about 30 kg/cm$^2$. Residence times in the reaction vessel or reaction zone can be varied as appropriate for given throughputs and conditions, with about 20 to about 150 minutes being generally suited to a range of processes. As will be appreciated by persons skilled in the manufacture of aromatic carboxylic acids, preferred conditions and operating parameters vary with different products and processes and can vary within or even beyond the ranges specified above.

Products obtained by oxidation of aromatic feed materials according to the invention include aromatic carboxylic acid derivatives of the aromatic feed material as well as less fully oxidized derivatives. By way of example, in the oxidation of para-xylene in aqueous acetic acid reaction solvent or water according to the invention, an oxidized product typically includes one or more para-xylene derivatives having at least one carboxylic acid substituent group having an alpha carbon atom, such as terephthalic acid, 4-carboxybenzaldehyde, p-toluic acid and p-hydroxymethylbenzoic acid, as well as one or more other oxidation products such as p-tolualdehyde, trimellitic acid, benzoic acid and 2, 4', 5-tricarboxybiphenyl. In embodiments of the invention in which a vapor phase is evaporated from the liquid reaction mixture for control of reaction temperature, major components of the vapor phase typically include water, which is generated as by-product of oxidation of the substituted aromatic feed material and may also be present as liquid medium for the reaction or a component thereof. The vapor phase will also include organic acid reaction solvent and oxidation by-products thereof if an organic acid solvent is used in the process. The vapor phase also typically contains lesser amounts of carbon monoxide and carbon dioxide, which can result from burning of aromatic feed material and, if present, organic acid reaction solvent. Aggregate carbon oxide (CO and $CO_2$) content of the vapor phase preferably is less than about 0.1 mole, and more preferably less than about 0.05 mole carbon oxides per mole of oxygen consumed in oxidation. The vapor phase may also contain minor amounts of unreacted aromatic feed material and oxidation products thereof and unreacted oxygen from gaseous oxygen sources together with inert gases that may be included in such sources. In preferred embodiments, aromatic feed material is converted to an oxidation product comprising one or more aromatic carboxylic acid derivatives of the feed material without substantial generation of carbon oxides. More preferably, carbon oxide levels in vent gases from the oxidation, including carbon oxides from burned aromatic feedstock as well as burned organic acid reaction solvent if used, are less than about one-half mole per mole of substituted aromatic feed material and still more preferably less than about 0.25 mole or 0.15 mole carbon monoxide plus carbon dioxide per mole of the feed material.

Oxidized product resulting from the invented process commonly is formed dissolved or as suspended solids in the liquid phase reaction mixture. Recovery of oxidized product or components thereof can be accomplished by any suitable technique. Solid product can be recovered from the liquid reaction medium by filtration techniques. Oxidized products present in the reaction medium both in solution and as suspended solids can be recovered conveniently by crystallization techniques. Aromatic carboxylic acid derivatives of the feed material are preferably recovered in solid form by crystallization from the reaction medium, which can be accomplished by cooling and releasing pressure on the liquid reaction mixture in the reaction zone or after removal therefrom. Solid product slurried in the liquid and/or solids crystallized from reaction liquid or from crystallization solvents are conveniently separated from the liquids by centrifuging, filtration or combinations thereof. Solid products recovered from the reaction liquid by such techniques comprise aromatic carboxylic acid derivatives of the aromatic feed material and other components of the oxidation product. If needed or desired, further separation of product species can be conducted by any suitable technique, such as solvent extraction, distillation or sublimation.

In some of its embodiments, features of the invented catalytic compositions and process, such as high conversions and carboxylic acid-selectivities, low carbon oxide generation, and performance even using water as a liquid reaction medium or solvents with relatively high water contents and in the complete or substantial absence of bromine, are especially suited to oxidation of aromatic feed materials comprising at least one dialkyl benzene, intermediate oxidation product thereof or combination thereof to aromatic carboxylic acids in high yields and at high selectivities to benzenedicarboxylic acids. Preferred processes according to such aspects of the invention comprise oxidation of aromatic feed materials comprising para-xylene or one or more intermediate oxidation products thereof or combinations thereof, to an oxidation product comprising terephthalic acid and oxidation of meta-xylene or one or more intermediate oxidation products thereof or combinations thereof to an oxidation products comprising isophthalic acid.

In such embodiments, the oxidation preferably comprises contacting the aromatic feed material with oxygen gas in a liquid phase reaction mixture which comprises water or water and acetic acid and has dissolved or slurried therein, or is otherwise contacted, such as in a fixed bed of supported or unsupported catalyst or catalyst component particles, with, a catalytic composition according to the invention at elevated temperature and pressure effective to maintain a liquid phase reaction mixture and preferably at a temperature of at least about 150 to about 230° C. Catalytic compositions according to the invention that are preferred for such processes exhibit conversions to oxidized product of at least about 80 mole % with selectivities to benzenedicarboxylic acid derivatives of the aromatic feed material of at least about 80% and more preferably with conversion, aromatic dicarboxylic acid selectivity or both of about 90% or more.

A particularly preferred catalytic composition according to the invention for such a process comprises a solid component comprising solid particles, comprising palladium and antimony in combination on the catalyst surface, and preferably in the form of an alloy, and optionally also comprising a minor amount, for example about 1 to about 5 atoms, bismuth or gold (or a combination thereof) per 10 atoms antimony, and also comprising a promoter which is an oxide or oxidizable form of molybdenum or another metal or metalloid and is present in solid form, either with particles of palladium and antimony or combinations of antimony and one or both of bismuth or gold, or separately therefrom, or is dissolved in the liquid oxidation reaction mixture.

Oxidation products of the liquid phase reaction in processes according to embodiments of the invention comprise aromatic carboxylic acids, and especially terephthalic acid or isophthalic acid, in good yield and with intermediate oxidation products and catalyst residues comprising palladium and at least one of antimony, bismuth and gold. Catalyst residues may also include a promoting metal or metalloid. Such catalyst residues are present in sufficiently low levels that the oxidation product is useful for conversion to pure forms of terephthalic acid or isophthalic acid if not for conversion directly to polyester suitable for melt spinning into fiber. A preferred terephthalic acid composition comprises terephthalic acid and, by weight thereof, about 0.001 to about 2000 ppmw palladium, calculated as the element, and about 0.001 to about 2000 ppmw antimony, bismuth, gold or combination thereof, calculated as elements, wherein palladium and at least one of antimony, bismuth and gold is present in the form of solid particles in which an atom ratio of palladium to antimony, bismuth, gold or a combination thereof is about 0.1:1 to about 10:1 and preferably about 1:1 to about 5:1. Such compositions also may contain about 0.001 to about 500 ppmw of at least one other metal or metalloid promoter for the palladium and antimony, bismuth or gold, and preferably a Group 4, 5 or 6 metal or metalloid, and most preferably, molybdenum, calculated as the element or a combination thereof. Terephthalic acid compositions according to a preferred embodiment of the invention comprises the acid and, by weight thereof, about 0.001 to about 100 ppmw palladium, calculated as the element, and about 0.001 to about 100 ppmw antimony, bismuth, gold or combination thereof, calculated as the element or elements, and preferably present in combination.

Pure forms of aromatic carboxylic acids produced according to the invention can be obtained, if purification is desired, by subjecting the oxidation product, either before or after recovery from the liquid phase reaction mixture, to lower temperature oxidation in one or more stages, such as described in U.S. Pat. Nos. 4,877,900, 4,772,748 and 4,286, 101. Preferred pure forms of terephthalic acid or isophthalic acid with lower impurities contents can made by catalytic hydrogenation of aqueous solutions of the oxidation product in the presence of a noble metal catalyst as described in U.S. Pat. No. 3,584,039. A preferred terephthalic acid composition according to the invention that is suitable for direct conversion by reaction with at least one glycol to polyester suitable for manufacture of fiber comprises terephthalic acid and, by weight thereof, less than about 100 ppmw 4-carboxybenzaldehyde, about 0.001 to about 100 ppmw palladium, calculated as the element, and about 0.001 to about 100 ppmw antimony, bismuth, gold or a combination thereof, calculated as elements, or a combination thereof, and preferably wherein at least a portion of the palladium is present and at least a portion of at least one of the antimony, bismuth and gold are present in combination in the form of particles.

The invention is described further in the following examples which are presented for purposes of non-limiting illustration and explanation.

COMPARATIVE EXAMPLES

For reference, a bromine-promoted cobalt-manganese catalyst representative of catalysts used in commercial manufacture of terephthalic acid by oxidation of para-xylene was tested in Comparative Example 1. Bromine-free compositions containing cobalt and zirconium as in US Patent Application No. 2002/0188155 were used in Comparative Examples 2-9.

For Comparative Example 1, cobalt (II) acetate tetrahydrate, manganese (II) acetate tetrahydrate and a solution of 48 wt % hydrobromic acid in water were added to a solvent containing 95 wt % acetic acid and 5 wt % water in amounts providing 615 parts per million by weight ("ppmw") cobalt, 616 ppmw manganese and 1120 ppmw bromine. The solution was loaded into a stirred 100 mL titanium reactor. The reactor was sealed, pressurized to 22 bara with compressed nitrogen and heated to maintain a constant temperature of 190° C. and, while maintaining those conditions, a gaseous mixture of 8 vol. % oxygen and 92 vol. % nitrogen was added continuously at a rate of 2.0 grams/minute and para-xylene (>99% pure) was added continuously at a rate of 0.133 gram/minute. After one hour, addition of para-xylene feed was stopped. Addition of the gaseous mixture was continued for an additional 30 minutes and then stopped. The reactor was cooled and a sample of the total reactor product slurry was removed and analyzed for terephthalic acid ("TA"), 4-carboxybenzaldehyde ("4CBA"), para-toluic acid ("PTOL") and para-tolualdehyde ("PTAL") by high pressure liquid chromatography ("HPLC"). Production of carbon oxides ("COx") was calculated based on concentrations in gas samples removed from the reactor during the last 30 minutes of para-xylene addition. Yields, in mole % based on para-xylene feed were, 98.1% TA, 0.4% 4CBA, 0.4% PTOL and 0.2% PTAL. Burning of acetic acid solvent and minor amounts of para-xylene feed generated 35 mole % COx based on mole of para-xylene feed.

For Comparative Examples 2-9, cobalt(II) acetate tetrahydrate and a solution of 16.2 wt % zirconyl(IV) acetate in water were added to an acetic acid and water solvent as in Comparative Example 1 in amounts providing varying levels of cobalt and zirconium at weight ratios of about 100:1, 10:1, 1:1 and 1:10 cobalt to zirconium, calculated as elements. The resulting compositions were loaded into a reactor as in Comparative Example 1 and, while maintaining a constant temperature of 195° C. and pressure of 22 bara, a nitrogen and oxygen mixture and para-xylene feed, both as in Comparative Example 1, were added continuously over a period of one hour at rates of 2.0 g/min. of the gas mixture and 0.133 g/min. para-xylene. Addition of para-xylene feed was discontinued after one hour and addition of the oxygen and nitrogen gas mixture was discontinued after another 30 minutes. Reactor contents were then cooled and total product was analyzed as in Comparative Example 1. Carbon oxide ("COx") production was calculated from vent gas samples taken during the last 30 minutes of para-xylene addition. Yields, in mole % based on para-xylene feed, ranged from 4.4-9.9% TA, 1.9-4.9% 4CBA, 36.9-49.5% PTOL, 3.0-7.8% PTAL. COx generation ranged from 103-204 mole % per mole para-xylene feed.

Example 1

Sample compositions were prepared by wet co-impregnations according to the following procedure. Precursor solutions of ammonium heptamolybdate, palladium(II) nitrate, and antimony(III) acetate were prepared by stirring in water at 60° C. weighed amounts of the salts and, in the case of the molybdenum and antimony salts, citric acid at a 2:1 weight ratio relative to the salts. Solution concentrations were 34% palladium(II) nitrate, 33% antimony(III) acetate, and 15% ammonium molybdate. For samples containing bismuth, a solution of bismuth(III) nitrate in water was used. Samples containing gold were prepared from basic $KAu(OH)_4$ solution. Supports in these examples were a mixed anatase and rutile phase titania powder having average primary particle size of 21 nm and BET surface area of about 60 $m^2/g$ identified as P25 from Degussa, a silica support in the form of free flowing white powder with surface area of 550 $m^2/g$, a carbon (graphite) support in the form of free flowing black powder with surface area of 280 $m^2/g$ and, for Sample No. 1-26, a powdered rutile titania support having rutile phase content of about 75-80 wt % and surface area of about 15-20 $m^2/g$. Samples were prepared by adding 6 mL. of the precursor salt solutions to 2-3 grams of support material to form wet slurries. In some cases additional water was added to the wet slurries to ensure even surface wetting. Solutions were placed in a porcelain dish and dried at 50° C. for 60 hours in an oven. Samples were then heated at a rate of 2° C./min to 120° C. and held at 120° C. for 2 hours. The dried samples were then calcined in a furnace heated at a rate of 0.4° C./min to 400-500° C. and held at the calcination temperature for 2 hours. Calcination temperatures are reported in Table 1 below. Titania- and silica-supported samples were calcined in air and carbon-supported samples in nitrogen. After calcining, the recovered solids were ground to powder, placed in a crucible, and reduced under flow of 7 vol. % hydrogen in nitrogen in a tube furnace at room temperature for 1 hour and then heated at a rate of 0.4° C./min to a final reduction temperature of 200-250° C., at which samples were held for 5 hours. Sample compositions and preparation conditions are reported in Table 1.

TABLE 1

| | | | Sample Treatment(s) | | |
|---|---|---|---|---|---|
| Sample No. | Support | Metal Loadings Wt. % Pd/Sb/Bi/Au/Mo | Steps: C = calcined R = reduced | Calcine Temp (° C.) and Gas | Red. temp (° C.) |
| 1-1 | Titania | 5/20/0/0/20 | C + R | 400-O2 | 200 |
| 1-2 | Titania | 5/10/0/0/20 | C + R | 400-O2 | 200 |
| 1-3 | Titania | 5/5/0/0/20 | C + R | 400-O2 | 200 |
| 1-4 | Titania | 5/2.5/0/0/20 | C + R | 400-O2 | 200 |
| 1-5 | Titania | 5/20/0/0/5 | C + R | 400-O2 | 200 |
| 1-6 | Titania | 5/10/0/0/5 | C + R | 400-O2 | 200 |
| 1-7 | Titania | 5/5/0/0/5 | C + R | 400-O2 | 200 |
| 1-8 | Titania | 5/2.5/0/0/5 | C + R | 400-O2 | 200 |
| 1-9 | Titania | 5/20/0/0/2.5 | C + R | 400-O2 | 200 |
| 1-10 | Titania | 5/10/0/0/2.5 | C + R | 400-O2 | 200 |
| 1-11 | Titania | 5/5/0/0/2.5 | C + R | 400-O2 | 200 |
| 1-12 | Titania | 5/2.5/0/0/2.5 | C + R | 400-O2 | 200 |
| 1-13 | Titania | 5/20/0/0/0.625 | C + R | 400-O2 | 200 |
| 1-14 | Titania | 5/10/0/0/0.625 | C + R | 400-O2 | 200 |
| 1-15 | Titania | 5/5/0/0/0.625 | C + R | 400-O2 | 200 |
| 1-16 | Titania | 5/2.5/0/0/0.625 | C + R | 400-O2 | 200 |
| 1-17 | Titania | 5.0/2.5/0/0/5 | C + R | 400-Air | 200 |
| 1-18 | Titania | 5.0/1/0/0/5 | C + R | 400-Air | 200 |
| 1-19 | Titania | 5.0/0.63/0/0/5 | C + R | 400-Air | 200 |
| 1-20 | Graphite | 5.0/0.63/0/0/5 | C | 400-N2 | — |
| 1-21 | Graphite | 2.5/0.5/0/0/2.5 | C + R | 400-N2 | 200 |
| 1-22 | Graphite | 2.5/0.5/0/0/2.5 | C + R | 500-N2 | 200 |
| 1-23 | Graphite | 5.0/1/0/0/5 | C + R | 500-N2 | 200 |
| 1-24 | Silica | 5.0/2.5/0/0 5.0 | C + R | 500-N2 | 200 |
| 1-25 | Graphite | 5.0/2.5/0/0/5 | C | 400-N2 | — |
| 1-26 | Rutile Titania | 5.0/2.5/0/0/5 | C + R | 500-N2 | 200 |
| 1-27 | Rutile Titania | 3.0/3.0/0.3/0/3.0 | C + R | 300-Air | 250 |
| 1-28 | Rutile Titania | 3.0/6.0/1.5/1.5/6.0 | C + R | 300-Air | 250 |
| 1-29 | Rutile Titania | 3.0/3.0/0/3.0/6.0 | C + R | 300-Air | 250 |
| 1-30 | Rutile Titania | 3.0/3.0/0/0/6.0 | C + R | 300-Air | 250 |

Oxidations with Samples 1-1 to –30 were conducted using a high temperature, high pressure, parallel batch reactor having 48 positions, each of which was fitted with an 8 mL disposable Teflon reactor sleeve equipped with magnetic stir bar. Samples and 1-1.5 mL of 10% para-xylene in water were added to each sleeve and the sleeves were fitted to the reactor, which was then sealed, pressured to 45 bar with air, and heated to 220° C. Reaction times varied as reported in Table 2. The reactor was cooled by immersion in ice, vented to relieve pressure, and 5 mL dimethyl sulfoxide ("DMSO") and an internal standard, 3-carboxybenzophenone, were added to each sleeve. The reactor was agitated to aid dissolution of products in the DMSO solution. Reactor sleeves were removed and their contents analyzed by HPLC. Table 2 reports ppmw metals and metalloids of the charged Samples; aggregate conversion of para-xylene to oxidized derivatives, TA, 4CBA, PTOL, PTAL, 4-hydroxylmethyl benzoic acid, 4-methyl benzoic acid and benzoic acid; TA yields based on para-xylene consumed; and TA selectivity based on the named derivatives.

TABLE 2

| Sample No. | Reaction Temp (° C.) | Time (minutes) | Pd/Sb/Bi/Au/Mo (ppmw) | PX Conv (%) | TA Selectivity (%) | TA Yield (%) |
|---|---|---|---|---|---|---|
| 1-1 | 220 | 60 | 1500/6000/—/—/6000 | 64.3 | 55.8 | 36.1 |
| 1-2 | 220 | 60 | 1500/3000/—/—/6000 | 89.9 | 94.5 | 86.4 |
| 1-3 | 220 | 60 | 1500/1500/—/—/6000 | 87.1 | 94.9 | 82.7 |
| 1-4 | 220 | 60 | 1500/750/—/—/6000 | 88.3 | 95.5 | 85.2 |
| 1-5 | 220 | 60 | 1500/6000/—/—/1500 | 89.6 | 82.0 | 74.6 |
| 1-6 | 220 | 60 | 1500/3000/—/—/1500 | 85.8 | 94.2 | 80.9 |
| 1-7 | 220 | 60 | 1500/1500/—/—/1500 | 85.0 | 91.2 | 78.5 |
| 1-8 | 220 | 60 | 1500/750/—/—/1500 | 83.9 | 94.6 | 80.3 |
| 1-9 | 220 | 60 | 1500/6000/—/—/750 | 71.6 | 70.8 | 50.8 |
| 1-10 | 220 | 60 | 1500/3000/—/—/750 | 82.0 | 97.4 | 79.9 |
| 1-11 | 220 | 60 | 1500/1500/—/—/750 | 85.5 | 85.2 | 73.0 |
| 1-12 | 220 | 60 | 1500/750/—/—/750 | 75.6 | 71.0 | 54.2 |
| 1-13 | 220 | 60 | 1500/6000/—/—/188 | 1.4 | 0.0 | 0.0 |
| 1-14 | 220 | 60 | 1500/3000/—/—/188 | 4.2 | 11.7 | 1.1 |
| 1-15 | 220 | 60 | 1500/1500/—/—/188 | 56.0 | 67.1 | 42.3 |
| 1-16 | 220 | 60 | 1500/750/—/—/188 | 32.1 | 71.4 | 28.3 |
| 1-17 | 220 | 60 | 1500/750/—/—/1500 | 95.1 | 93.9 | 89.3 |
| 1-18 | 220 | 30 | 750/150/—/—/750 | 84.9 | 88.2 | 74.8 |
| 1-19 | 220 | 30 | 1500/189/—/—/1500 | 86.2 | 83.2 | 71.7 |
| 1-20 | 220 | 30 | 1500/189/—/—/1500 | 74.9 | 67.3 | 50.4 |
| 1-21 | 220 | 30 | 750/150/—/—/750 | 93.1 | 74.0 | 68.9 |
| 1-22 | 220 | 30 | 750/150/—/—/750 | 90.8 | 72.4 | 65.7 |
| 1-23 | 220 | 30 | 1500/300/—/—/1500 | 80.5 | 78.1 | 62.8 |
| 1-24 | 220 | 30 | 1500/750/—/—/1500 | 26.0 | 96.0 | 25.0 |
| 1-25 | 220 | 60 | 3000/1500/—/—/3000 | 86.0 | 93.0 | 80.0 |
| 1-26 | 220 | 60 | 3000/1500/—/—/3000 | 86.0 | 96.0 | 82.6 |
| 1-27 | 210 | 90 | 900/900/90/—/900 | 100.0 | 99.5 | 81.7 |
| 1-28 | 210 | 90 | 900/1800//450/450/1800 | 100.0 | 99.0 | 82.1 |
| 1-29 | 210 | 90 | 900/900/—/900/1800 | 100.0 | 98.7 | 88.8 |
| 1-30 | 210 | 90 | 900/900/—/—/1800 | 43.6 | 1.9 | 0.1 |

Examples 2-6

Compositions were prepared according to the procedure of Example 1 but with the metal salt solutions added to the support either alone or with another metal component, as reported more specifically in Table 3. The titania support used in Examples 2-6 was the mixed anatase and rutile titania used in Example 1. Citric acid was used with molybdenum and antimony salt solutions. Samples were dried and calcined between the steps of the preparation sequence. Slurries were dried slowly for 12 hours or more at 70° C. in an oven and temperatures were then increased at 2° C./min to 120° C. and held there for 3 hours. Samples were calcined in air in a furnace by heating with increases of 1° C. per minute from room temperature to 400° C. and then holding at that temperature for 2 hours. The calcined samples were then ground to fine powder prior to reduction or the next addition step. Sample formulations and yields of terephthalic acid in oxidation trials conducted as in Example 1 are shown in Table 3. Precursor solutions were added to supports in sequences shown in the "Addition Order" column of the table reading from left to right. Separate additions of the solutions are designated with slash marks ("/") and additions of two or more solutions together in single steps are designated by plus signs ("+").

TABLE 3

| Example | Metal Loadings (wt %) | | | Addition Order | PX Conversion | TA Selectivity |
|---|---|---|---|---|---|---|
| | Pd | Sb | Mo | | | |
| 2 | 5 | 5 | 5 | Sb/Pd + Mo | 80 | 98 |
| 3 | 5 | 5 | 5 | Pd + Mo + Sb | 81 | 97 |
| 4 | 2 | 2 | 2 | Mo/Pd + Sb | 76 | 97 |
| 5 | 2 | 2 | 2 | Sb/Pd/Mo | 77 | 95 |
| 6 | 2 | 2 | 2 | Pd + Sb/Mo | 55 | 80 |
| Comp. Ex. 10 | 5 | 5 | 5 | Mo + Sb/Pd | 0 | 0 |
| Comp. Ex. 11 | 5 | 5 | 5 | Sb/Mo/Pd | 0 | 0 |
| Comp. Ex. 12 | 5 | 5 | 5 | Mo/Pd/Sb | 0 | 0 |

Examples 7-33

Samples were prepared with step-wise impregnations following procedures as in Examples 2-6 and tested in oxidation trials following the procedure of Example 1 except that reaction times were 90 minutes and palladium concentrations were 1500 ppmw in trials with samples from Examples 7-29 and 600 ppmw in trials with samples from Examples 30-33. Precursor solutions of metal salts were added in either one or two impregnation steps with drying and calcination between steps. The samples were reduced as described in Examples 2-6 with reduction temperatures ranging from 200-350° C. Sample preparations and results of oxidation trials are reported in Table 4. PX Conversion values in trials using samples 25 and 33 exceeded the theoretical limit of 100% due to rounding off of measurements.

TABLE 4

| Example No. | Pd wt % | Pd:Sb:Mo wt Ratio | Impregnation Steps 1 | Impregnation Steps 2 | Red. Temp (°C.) | PX Conv (%) | Sel TA (%) | Yield TA (%) |
|---|---|---|---|---|---|---|---|---|
| 7 | 5 | 1:1:1 | Pd + Sb + Mo | None | 200 | 90 | 90 | 81 |
| 8 | 5 | 1:1:1 | Pd + Sb + Mo | None | 250 | 87 | 95 | 84 |
| 9 | 5 | 1:1:1 | Pd + Sb + Mo | None | 300 | 88 | 97 | 85 |
| 10 | 5 | 1:1:1 | Pd + Sb + Mo | None | 350 | 88 | 97 | 86 |
| 11 | 5 | 1:1:2 | Pd + Sb + Mo | None | 200 | 86 | 98 | 85 |
| 12 | 5 | 1:1:2 | Pd + Sb + Mo | None | 250 | 85 | 97 | 83 |
| 13 | 5 | 1:1:2 | Pd + Sb + Mo | None | 300 | 87 | 79 | 70 |
| 14 | 5 | 1:1:2 | Pd + Sb + Mo | None | 350 | 84 | 84 | 71 |
| 15 | 5 | 1:2:1 | Pd + Sb + Mo | None | 200 | 86 | 96 | 83 |
| 16 | 5 | 1:2:1 | Pd + Sb + Mo | None | 250 | 88 | 95 | 83 |
| 17 | 5 | 1:2:1 | Pd + Sb + Mo | None | 300 | 88 | 96 | 85 |
| 18 | 5 | 1:2:1 | Pd + Sb + Mo | None | 350 | 87 | 93 | 81 |
| 19 | 5 | 1:1:1 | Pd + Sb | Mo | 200 | 87 | 97 | 86 |
| 20 | 5 | 1:1:1 | Pd + Sb | Mo | 250 | 88 | 97 | 87 |
| 21 | 5 | 1:1:1 | Pd + Sb | Mo | 300 | 89 | 94 | 84 |
| 22 | 5 | 1:1:1 | Pd + Sb | Mo | 350 | 89 | 94 | 85 |
| 23 | 5 | 1:1:2 | Pd + Sb | Mo | 200 | 87 | 97 | 84 |
| 24 | 5 | 1:1:2 | Pd + Sb | Mo | 250 | 100 | 95 | 95 |
| 25 | 5 | 1:1:2 | Pd + Sb | Mo | 350 | 102 | 96 | 98 |
| 26 | 5 | 1:2:1 | Pd + Sb | Mo | 200 | 88 | 93 | 83 |
| 27 | 5 | 1:2:1 | Pd + Sb | Mo | 250 | 86 | 99 | 85 |
| 28 | 5 | 1:2:1 | Pd + Sb | Mo | 300 | 87 | 97 | 85 |
| 29 | 5 | 1:2:1 | Pd + Sb | Mo | 350 | 89 | 95 | 85 |
| 30 | 2 | 1:1:1 | Pd + Sb | Mo | 200 | 87 | 92 | 80 |
| 31 | 2 | 1:1:2 | Pd + Sb | Mo | 300 | 88 | 96 | 85 |
| 32 | 2 | 1:2:1 | Pd + Sb | Mo | 200 | 89 | 96 | 87 |
| 33 | 2 | 1:2:1 | Pd + Sb | Mo | 300 | 101 | 96 | 97 |

Examples 34-39

Samples were prepared following the procedure of Example 1. Sample compositions are reported in Table 5.

TABLE 5

| Sample | Support | Pd (Wt %) | Sb (Wt %) | Mo (Wt %) | Metals on Catalyst |
|---|---|---|---|---|---|
| Comp. Ex. 13 | Titania | 5 | | | Pd |
| Comp. Ex. 14 | Titania | | 5 | | Sb |
| Comp. Ex. 15 | Titania | | | 5 | Mo |
| Ex. 34 | Titania | 5 | 5 | | Pd + Sb |
| Comp. Ex. 16 | Titania | | 5 | 5 | Sb + Mo |
| Comp. Ex. 17 | Titania | 5 | | 5 | Pd + Mo |

The sample compositions were used in oxidation trials following the procedure of Example 1. Results, including averages for multiple runs using the individual samples, are reported in Table 6.

TABLE 6

| Trial No. | Samples Used | Reactor Pd Concentration (ppmw) | Reactor Pd:Sb:Mo wt ratio | Conv % | Sel TA % | TA Yield |
|---|---|---|---|---|---|---|
| Comp. Ex. 18 | Comp. Ex. 13, 14 and 15 | 1500 | 1:1:1 | 33 | 55 | 22 |
| Comp. Ex. 19 | Comp. Ex. 13, 14 and 15 | 1500 | 1:1:1 | 36 | 57 | 25 |
| Comp. Ex. 20 | Comp. Ex. 13, 14 and 15 | 1500 | 1:1:1 | 40 | 51 | 24 |
| | Average of Comp. Ex. 18-20 | | | 36 | 54 | 24 |
| Ex. 35 | Ex. 34 and Comp. Ex. 15 | 1500 | 1:1:1 | 84 | 94 | 80 |

TABLE 6-continued

| Trial No. | Samples Used | Reactor Pd Concentration (ppmw) | Reactor Pd:Sb:Mo wt ratio | Conv % | Sel TA % | TA Yield |
|---|---|---|---|---|---|---|
| Ex. 36 | Ex. 34 and Comp. Ex. 15 | 1500 | 1:1:1 | 83 | 95 | 80 |
| Ex. 37 | Ex. 34 and Comp. Ex. 15 | 1500 | 1:1:1 | 84 | 96 | 81 |
| Ex. 38 | Ex. 34 and Comp. Ex. 15 | 1500 | 1:1:1 | 85 | 97 | 83 |
| Ex. 39 | Ex. 34 and Comp. Ex. 15 | 1500 | 1:1:1 | 82 | 96 | 79 |
| | Average of Ex. 35-39 | | | 84 | 96 | 81 |
| Comp. Ex. 21 | Comp. Ex. 13 and 16 | 1500 | 1:1:1 | 80 | 75 | 60 |
| Comp. Ex. 22 | Comp. Ex. 13 and 16 | 1500 | 1:1:1 | 76 | 74 | 57 |
| Comp. Ex. 23 | Comp. Ex. 13 and 16 | 1500 | 1:1:1 | 79 | 76 | 60 |
| Comp. Ex. 24 | Comp. Ex. 13 and 16 | 1500 | 1:1:1 | 78 | 76 | 60 |
| | Average of Comp. Ex. 21-24 | | | 78 | 75 | 59 |
| Comp. Ex. 25 | Comp. Ex. 14 and 17 | 1500 | 1:1:1 | 84 | 89 | 75 |
| Comp. Ex. 26 | Comp. Ex. 14 and 17 | 1500 | 1:1:1 | 84 | 89 | 76 |
| Comp. Ex. 27 | Comp. Ex. 14 and 17 | 1500 | 1:1:1 | 82 | 94 | 77 |
| Comp. Ex. 28 | Comp. Ex. 14 and 17 | 1500 | 1:1:1 | 82 | 94 | 79 |
| Comp. Ex. 29 | Comp. Ex. 14 and 17 | 1500 | 1:1:1 | 68 | 95 | 65 |
| Comp. Ex. 30 | Comp. Ex. 14 and 17 | 1500 | 1:1:1 | 81 | 93 | 75 |
| | Average of Comp. Ex. 25-30 | | | 80 | 92 | 74 |

Example 40

Selected samples from previous Examples and Comparative Examples were characterized by electron microscopy. Some of the samples were characterized before use in oxidation trials. Others were isolated from reaction mixtures after oxidation trials. The analyses are described more fully below and results are reported in Table 7.

As-received fresh and used samples were prepared for SEM analyses by drop-dispersion casting onto specimen holders. Approximately 10 micrograms of sample material (e.g., a micro-spatula tip-full quantity) were suspended in <1 mL absolute ethanol within a 1-dram borosilicate, Teflon-capped vial. Suspensions were then sonicated within a Branson 1210 sonicator for 25 seconds. 5 microliters of the suspensions were pipetted onto a 3 mm holey carbon coated copper TEM grid (400 mesh; supplied by SPI Inc.) and allowed to dry.

Samples were microanalyzed using a FEI Nova 600 NanoSEM with the microscope operated in high vacuum mode using an Immersion Lens and multiple imaging detectors and modes. Secondary electron images (SEI) with topographical contrast were generated with an in-lens or through-lens detector (tld). Backscattered electron images (BEI) with atomic number contrast were formed using solid state, annular ring BSED mounted on the bottom of the pole piece. Digital BEI micrographs magnified from ×150,000 to ×1,000,000 were obtained. These images showed higher atomic number palladium and antimony particles as bright features on slightly darker titania support particles.

Elemental analyses were performed by energy dispersive spectroscopy (EDS) using either a high spectral resolution SiLi detector, high throughput SDD detector, or both. EDS spectra were collected on the NanoSEM using an accelerating voltage of 10 kV with a spot size of 3.5. Relative metals concentrations were determined using a Noran System Six software package and Proza standardless calibration from ThermoElectron Corporation. The electron beam was used in a spot or stationary probe mode and was held on a metal particle for 60 seconds or more. Pd/Sb atom ratios were calculated from atom % results from the EDS spectrum using the Proza standardless analysis.

Average sizes of palladium-antimony particles were measured directly from digital images using NIH image analysis software, ImageJ. TIFF images were opened in ImageJ, and scale-calibrated using the image scale bar as the scale reference. Statistical evaluations of data sets (minimum 25 representative particles) were performed using MS Excel to yield average particle sizes.

The BEI micrographs were used for metal particle measurements and to provide estimates of the extent or quality of metal dispersions. Dispersions were categorized as high, medium, or poor. High dispersion reflects a uniform and homogeneous distribution of fine metal or metalloid particles. Poor dispersion reflects a heterogeneous distribution, with widely varying size, including larger particles or clusters and localized concentration. Medium dispersion reflects a relatively uniform range in particle-size, but with some local concentration or gathering of metal particles in association with titania particles or clusters thereof.

TABLE 7

| | | | | | | Pd/Sb Particles | |
|---|---|---|---|---|---|---|---|
| Example | Type | Support | TA Yield (%) | TA Sel. (%) | Particle Dispersion | Atomic Pd/Sb Ratio | Ave. Pd/Sb particle size (nm) |
| Ex. 2 | Fresh | titania | 80 | 98 | high | 1.9 | 7.2 |
| Ex. 3 | Fresh | titania | 81 | 97 | high | 1.4 | 8.5 |

TABLE 7-continued

| | | | | | Pd/Sb Particles | | |
|---|---|---|---|---|---|---|---|
| Example | Type | Support | TA Yield (%) | TA Sel. (%) | Particle Dispersion | Atomic Pd/Sb Ratio | Ave. Pd/Sb particle size (nm) |
| Ex. 5 | Fresh | titania | 77 | 95 | high | 2.7 | 7.5 |
| Ex. 6 | Fresh | titania | 55 | 80 | high | 4.7 | 7.9 |
| Comp. Ex. 10 | Fresh | titania | 0 | 0 | poor | 3.0 | >100 |
| Comp. Ex. 11 | Fresh | titania | 0 | 0 | poor | 1.7 | >100 |
| Comp. Ex. 12 | Fresh | titania | 0 | 0 | poor | 1.7 | >100 |
| 1-24 | Fresh | silica | 25 | 96 | high | 2.9 | 12.2 |
| 1-25 | Fresh | carbon | 74 | 70 | high | 2.5 | 5.8 |
| 1-26 | Fresh | rutile titania | 83 | 96 | high | 2.0 | 6.4 |
| Comp. Ex. 18-20 | Used | titania | 24 | 54 | discrete | 9.2 | 13.5 |
| Ex. 34-38 | Used | titania | 81 | 96 | discrete | 1.5 | 8.2 |
| Comp. Ex. 21-24 | Used | titania | 59 | 75 | discrete | 2.9 | 10.9 |
| Comp. Ex. 25-30 | Used | titania | 74 | 92 | high | 2.2 | 12.2 |

As seen from the table, fresh and used samples that performed best in oxidation trials were characterized by very small palladium and antimony rich particles, typically smaller than 25 nm, which were typically highly dispersed on the support or clustered as discrete particles in regions of the support. Samples that performed poorly in oxidation trials either lacked particles rich in palladium and antimony or contained palladium and antimony in agglomerates. In samples that performed the best in oxidation trials, palladium to antimony atom ratios in particles was about 1:1 to 3:1. Higher ratios appeared to reduce selectivity of samples to TA. Molybdenum, as well as antimony not associated with palladium appeared to be distributed predominantly on support surfaces. Similar structures were seen with the different support materials used in preparing samples.

Example 41-43

Samples in Examples 41 and 42 were prepared by wet co-impregnation using a 34 weight % solution prepared by dissolving 64.1 g of palladium(II) nitrate with 124.2 g water, a solution prepared by dissolving 145.2 g citric acid monohydrate and 72.6 g antimony(III) acetate in 300 g water at 60° C. and allowing the result to cool to room temperature, and a solution prepared by dissolving 27.2 g ammonium heptamolybdate and 54.5 g citric acid monohydrate in 100 g of water and allowing the result to cool to room temperature. These solutions were combined and 500 g titania, designated P25 from DeGussa, were added with stirring. The titania was added in 50 g portions. Water was added to prevent the solution from becoming too viscous during addition of the titania until total volume of the mixture was 2 liters. The slurry was stirred for 8-12 hours at 50° C. and then portions were transferred to nine 250 mL porcelain dishes and left to dry in an oven at 60° C. for at least 48 hours. After drying, samples were heated to 120° C. and held at that temperature for 2 hours. Samples were then heated in a furnace to 400° C. at a rate of 0.5° C./min and held at temperature for 2 hours. The samples were cooled to room temperature and ground to yield 579 g of fine powder. This powder was reduced in six 75-95 g batches with 2-3 g of powder per crucible under flow of 7 vol % hydrogen in nitrogen at a rate of 100 mL/min by heating the samples with temperature increasing at a rate of 1° C./min to 250° C. and holding at that temperature for 5 hours.

Samples were used in para-xylene oxidation trials using a 300 mL titanium Parr reaction vessel. The vessel was is equipped with a Magnadrive stirrer and 2 water-jacketed condensers. The reactor setup had 2 pumps for liquid additions during operation; one for feeding distilled water and the other for delivery of para-xylene feed. Premixed gas cylinders containing approximately 8 vol % oxygen were used in semi-continuous trials. These trials were conducted at 550 psig total reactor pressure, reaction temperature of 200-210° C., para-xylene feedstock flow rate of 0.27 mL/min and water flow rate of 0.28 mL/min. The 8% oxygen feed rate was initially 4 standard cubic feet/hour (SCFH) and was periodically increased during the first 39 minutes of the runs to a maximum of 9 SCFH. Run times were 60 minutes plus 15 minute tailout periods during which feedstock addition was stopped but the 8% oxygen flow was continued. Conditions during trials were monitored using a computerized data-logging system.

For the oxidation trials, the reactor bottom was charged with 5.85 g of catalyst and 110 g distilled water. The reactor was sealed, and the stirrer was started at a speed of about 200 RPM. After a few minutes, the stirrer speed was increased to 500 RPM and nitrogen flow was started at a rate of 4 SCFH. The reactor was pressured to 550 psi. After the pressure set point was reached, stirrer speed was increased to 700 RPM and the reactor was heated to 210° C. When the internal temperature reached 204° C., or after one hour, a 20-minute timer was started. With 30-seconds remaining on the timer, the timer on a data-logging computer was started. When the timer reached zero, the reaction was initiated by quickly turning on the para-xylene feed pump, increasing stirrer speed to 1000 RPM and starting a timer to log the reaction time. Three minutes into the reaction time, the gas flow was switched from nitrogen to the 8% oxygen in nitrogen mixture. After 6 minutes, the water flow was started by turning on the pump. Gas flow rate was increased in 1 SCFH increments according to Table 8 below. The feed gas flow set point was set to the maximum of 9 SCFH at 39 minutes into the run. This flow rate was unchanged until the run was completed.

TABLE 8

| Time (minutes from reaction initiation) | Feed gas flow rate set point (SCFH) |
|---|---|
| 0 | 4 |
| 9 | 5 |
| 18 | 6 |
| 24 | 7 |
| 30 | 8 |
| 39 | 9 |

Reactions were continued for 60 minutes during which the $O_2$, $CO_2$, and CO of the vent gas were analyzed and recorded at 3 minute intervals. Temperatures and pressures of the reactor were also recorded. The feedstock pump was turned off at the 60-minute mark. Reactions continued with 8% oxygen/nitrogen feed gas and the water flow during 15-minute tailout periods. Upon run completion, the feed gas was switched from 8% oxygen/nitrogen to pure nitrogen, the water pump and temperature controller were turned off, and the gas flow set point was returned to 4 SCFH.

The reactor was cooled, vented and opened. The total reactor effluent (TRE) was collected into a tared sample jar. A representative TRE sample was retrieved and analyzed by HPLC. Overhead condensate was withdrawn from the trap on the reactor and its weight recorded. Following the oxidation trial using the sample prepared in Example 42, the product mixture from the trial was heated in an autoclave in water to 230° C. to dissolve terephthalic acid. The remaining residue was collected on a 0.2 micron sintered titanium metal filter. This material was then reduced at 350° C. under hydrogen for 2 hours and is designated Example 43. Data from these runs are reported in Table 9.

TABLE 9

| Example | Reaction Time (primary + secondary) (mins) | Total COx (moles) | O2 Consumed (moles) | Avg. vent (% O2) | TA yield (mole %) | TA Sel. (%) | Initial Catalyst |
|---|---|---|---|---|---|---|---|
| 41 | 90 + 3 | 0.07 | 0.71 | 3.94 | 63.8 | 81.7 | Fresh |
| 42 | 90 + 3 | 0.06 | 0.76 | 3.14 | 88.1 | 95.6 | Fresh |
| 43 | 90 + 3 | 0.05 | 0.73 | 1.95 | 76.4 | 89.0 | Used |

Samples from Examples 41-43 were analyzed for metal loadings by inductively coupled plasma optical emission spectroscopy ("ICP-OES") and for metal surface area by CO chemisorption using a Micromeritics 2010 analyzer using a Pd to CO ratio of 1. Microscopic characteristics of the samples were analyzed using a FEI Co. NanoSEM 600 field emission scanning electron microscope (FE-SEM) fitted with a ThermoElectron EDS spectrometer as in Example 40. High resolution transition electron microscope images were collected on a JEOL 2100F Cs-corrected TEM and an FEI Titan aberration-corrected transition electron microscope using conventional imaging methodology. Analyses of the samples showed palladium on the sample surface in small particles also containing antimony. The average size of the particles and the average palladium/antimony atom ratio of the particles are reported in Table 10. Presence of palladium and antimony in the form of an alloy in the palladium-antimony particles was indicated by observation of lattice fringe spacings corresponding to the (100) and (102) lattice planes and correlation to the (100) and (102) spacings within known palladium-antimony alloys as reported in international Tables for Crystallography. Vol. A, Space Group Symmetry. Hahn, T. (ed.). 4$^{th}$ edition, Kluwer Academic Publishers, Dordrecht, 1995. Pd/Sb particles in the samples were observed preferentially on anatase phases in the titania support particles. Antimony not found mixed with palladium was observed in a fine layered structure on support surfaces. Molybdenum was observed as small surface particles, average sizes of which appear in the table.

TABLE 10

| Example | Metal Composition | | | Active Metal Surface Area (m2 Pd/g cat) | Ave. Pd/Sb Particle Size (nm) | Ave. Pd/Sb Particle Atom Ratio | Ave. Mo Particle Size (nm) |
|---|---|---|---|---|---|---|---|
| | Pd | Sb | Mo | | | | |
| 41 | 5.2 | 4.8 | 2.6 | 2.30 | 7.3 | 2.1 | 1.2 |
| 42 | 5.1 | 4.9 | 2.5 | 2.2 | 6.6 | 1.3 | Not measured |
| 43 | 5.1 | 3.4 | 2.4 | Not measured | 10.6 | 1.8 | Not measured |

We claim:

1. A process for conversion of an aromatic feedstock to an oxidized aromatic product comprising at least one aromatic carboxylic acid comprising contacting an aromatic feedstock comprising a substituted aromatic hydrocarbon having at least one oxidizable substituent group with oxygen in a liquid reaction mixture comprising the aromatic feedstock, oxygen, water, not more than 10 wt. % $C_{1-8}$ monocarboxylic acid, and a catalyst composition comprising palladium and at least one of antimony, bismuth and gold, wherein particles dispersed on a surface of the catalyst comprise at least a portion of the palladium in combination with at least a portion of at least one of antimony, bismuth or gold, to convert the aromatic feedstock to an oxidized aromatic product comprising at least one aromatic carboxylic acid.

2. The process of claim 1 wherein the particles of the catalyst composition comprise palladium, antimony and at least one of bismuth and gold.

3. The process of claim 1 wherein the catalyst composition additionally comprises an oxide or oxidizable form of at least one metal or metalloid that is effective to improve the conversion or selectivity of palladium and at least one of antimony, bismuth or gold for oxidation of the substituted aromatic hydrocarbon to aromatic carboxylic acid.

4. The process of claim 3 wherein the metal or metalloid in oxide or oxidizable form is present in solid form in the liquid reaction mixture.

5. The process of claim 3 wherein the metal or metalloid in oxide or oxidizable form is present in solution in the liquid reaction mixture.

6. The process of claim 1 wherein the catalyst comprises an oxide or oxidizable form of at least one Group 4, 5 or 6 metal or metalloid.

7. The process of claim 1 wherein the catalyst additionally comprises an oxide or oxidizable form of molybdenum.

8. The process of claim 1 wherein the aromatic feedstock comprises para xylene.

9. The process of claim 1 wherein the aromatic feedstock comprises para-xylene or a partially oxidized derivative thereof.

10. The process of claim 9 wherein the catalyst additionally comprises an oxide or oxidizable form of molybdenum.

11. The process of claim 9 wherein conversion of the para xylene or partially oxidized derivative to oxidized derivatives is at least about 80 mole %.

12. The process of claim 11 wherein selectivity to carboxylic acid is at least 80%.

13. The process of claim 1 wherein the aromatic feedstock comprises meta-xylene or a partially oxidized derivative thereof.

14. The process of claim 1 wherein the catalyst comprises a solid component comprising solid particles comprising palladium and antimony or a combination of antimony and bismuth, and an oxide or oxidizable form of molybdenum.

15. The process of claim 1 wherein the oxide or oxidizable form of molybdenum is present in solid form.

16. The process of claim 14 wherein the oxide or oxidizable form of molybdenum is present in solid form with the solid particles comprising palladium and antimony or antimony and bismuth.

17. The process of claim 14 wherein the oxide or oxidizable form of molybdenum is present in solid form separate from the particles comprising palladium and antimony or antimony and bismuth.

18. The process of claim 14 wherein the oxide or oxidizable form of molybdenum is present dissolved in the liquid reaction mixture.

* * * * *